(12) United States Patent
Selvester et al.

(10) Patent No.: US 6,230,048 B1
(45) Date of Patent: May 8, 2001

(54) PICTORIAL-DISPLAY ELECTROCARDIOGRAPHIC INTERPRETATION SYSTEM AND METHOD

(75) Inventors: Ronald H. Selvester, Long Beach, CA (US); Joseph C. Solomon, Merrill; Peter M. Galen, McMinnville, both of OR (US)

(73) Assignee: Inovise Medical, Inc., Newberg, OR (US)

( * ) Notice: Subject to any disclaimer, the term of this patent is extended or adjusted under 35 U.S.C. 154(b) by 0 days.

(21) Appl. No.: 09/397,346

(22) Filed: Sep. 15, 1999

Related U.S. Application Data
(60) Provisional application No. 60/100,736, filed on Sep. 17, 1998.

(51) Int. Cl.[7] ........................................ A61B 5/04
(52) U.S. Cl. ............................................. 600/523
(58) Field of Search ...................... 600/523, 509

(56) References Cited

U.S. PATENT DOCUMENTS

| | | |
|---|---|---|
| 4,812,976 | 3/1989 | Lundy . |
| 4,898,181 | 2/1990 | Kessler . |

(List continued on next page.)

OTHER PUBLICATIONS

The Selvester QRS Scoring System for Estimating Myocardial Infarct Size, The Development and Application of the System, *Electrocardiography for the Clinician*, Arch Intern Med, vol. 145, pp. 1877–1881, Oct. 1985.

*Evaluation of a QRS Scoring System for Estimating Myocardial Infarct Size*, V. Specificity and Method of Application of the Complete System, The American Journal of Cardiology, vol. 55, pp. 1485–1490, Jun. 1, 1985.

*Quantitative QRS Criteria for Diagnosing and Sizing Myocardial Infarcts*, The American Journal of Cardiology, vol. 53, pp. 875–878, Mar. 1, 1984.

*The QRS Scoring System for Estimating Myocardial Infarct Size: Clinical, Angiographic and Prognostic Correlations*, Journal of American College of Cardiology, vol. 2, No. 1, pp. 38–44, Jul. 1983.

*Evaluation of a QRS Scoring System in Acute Myocardial Infaction: Relation to Infrarct Size, Early Stage Left Ventricular Ejection Fraction, and Exercise Performance*, The American Journal of Cardiology, vol. 52, pp. 37–42, Jul. 1983.

*Evaluation of a QRS Scoring System for Estimating Myocardial Infarct Size, I. Specificity and Observer Agreement*, Circulation, vol. 65, No. 2, pp. 342–347, Feb. 1982.

*A QRS Scoring System for Assessing Left Ventricular Function After Myocardial Infarction*, The New England Journal of Medicine, vol. 306, No. 1, pp. 4–9, Jan. 7, 1982.

16, *Myocardial Infarction*, Comprehensive Electrocardiology, vol. 1 (date unknown), pp. 565–629.

(List continued on next page.)

Primary Examiner—Scott M. Getzow
(74) *Attorney, Agent, or Firm*—Kolisch, Hartwell, Dickinson, McCormack & Heuser

(57) ABSTRACT

A computer-based electrocardiointerpretation system and method wherein subject-specific ECG data is interpreted in accordance with a set of interpretation rules to identify the presence(s), and certain characteristics, of various selected heart conditions. Detected conditions are presented for viewing as markers on a generally representational pictorial view of the heart. Interpretation is performed using some or all of the following kinds of information: hypertrophy information; general population reference physiological/anatomical data; and subject-specific physiological/anatomical and medical-history data.

28 Claims, 9 Drawing Sheets

U.S. PATENT DOCUMENTS

| | | |
|---|---|---|
| 5,687,737 | 11/1997 | Branham et al. . |
| 5,803,084 | 9/1998 | Olson . |
| 5,819,741 | 10/1998 | Karlsson et al. . |

OTHER PUBLICATIONS

*Factors Influencing Infarct Size Following Experimental Coronary Artery Occlusions*, Circulation, vol. XLIII, Jan., 1971, pp. 67–82.

*I. The Normal Heart*, Simulation Studies of the Electrocardiogram, vol. 43, No. 2, Aug., 1978, pp. 301–315.

*Computer Simulation of the Electrocardiogram*, Computer Techniques in Cardiology, Chapter 13, 1979, pp. 417–453.

*ST Isopotential Precordial Surface Maps in Patients with Acute Myocardial Infarction*, J. Electrocardiology, vol. 12, No. 1, 1979, pp. 55–64.

*Clinically Practical Lead Systems for Improved Electrocardiography: Comparison with Precordial Grids and Conventional Lead Systems*, Circulation, vol. 59, No. 2, Feb. 1979, pp. 356–363.

*II. Methods for Determining Infarct Size*, Myocardial Infarction Measurement and Intervention, 1982, pp. 23–50.

*Pathological Validation of Computer Model Criteria for Localizing Infarct in 12 Segments of L.V.*, Proceedings of the 1982 Engineering Foundation Conference Computerized Interpretation of the Electrocardiogram, May 9–14–, 1982, Miramar Hotel, pp. 127–138.

*Evaluation of a QRS Scoring System for Estimating Myocardial Infarct Sice. II. Correlation With Quantitative Anatomic Findings for Anterior Infarct*, The American Journal of Cardiology, May, 1982, vol. 49, pp. 1604–1613.

*Evaluation of QRS Scoring System for Estimating Myocardial Infarct Size. III. Correlation with Quantitative Anatomic Findings for Inferior Infarcts*, The American Journal of Cardiology, Feb. 1983, vol. 51, pp. 382–389.

*Evaluation of QRS Scoring System for Estimating Myocardial Infarct Size. IV. Correlation with Quantitative Anatomic Findings for Posterolateral Infarcts*, The American Journal of Cardiology, Mar. 1, 1984, vol. 53, pp. 706–714.

*11. Computerized Quantitative Electrocardiography: Potential Roles in Evaluating the Cardiac Patient*, 1987, pp. 177–190.

*Mathematical Modeling of Electrical Activity of the Heart*, J. Electrocardiology, vol. 20, No. 3, 1987, pp. 219–226.

*Fine Grid Computer Simulation of QRS–T and Criteria for the Quantitation of Regional Ischemia*, J. Electrocardiology Supplemental Issue, Oct. 1987, pp. 1–8.

*Transient Alterations of the QRS Complex and ST Segment During Percutaneous Transluminal Balloon Angioplasty of the Left Anterior Descending Coronary Artery*, The American Journal of Cardiology, Nov. 15, 1988, vol. 62, pp. 1038–1042.

*Ventricular Excitation During Percutaneous Transluminal Angioplasty of the Left Anterior Descending Coronary Artery*, The American Journal of Cardiology, vol. 62, pp. 1116–1121.

*16–Lead ECG Changes with Coronary Angioplasty, Location of ST–T Changes with Balloon Occlusion of Five Arterial*, Journal of Electrocardiology, vol. 24 Supplement, 1991, pp. 153–162.

*Electrocardiographic Diagnosis of Left Ventricular Hypertrophy in the Presence of Bundle Branch Block*, American Heart Journal, vol. 122, No. 3, Part 1, Sep., 1991, pp. 818–822.

*Optimial ECG Electrode Sites and Criteria for Detection of Asymptomatic Coronary Artery Disease—Update 1990, Multilead ECG Changes at Rest, With Exercise, and with Coronary Angioplasty*, Aerospace Medicine Directorate, Feb., 1992, pp. 8–18.

*FDA Approves Test Developed at MIT to Predict Sudden Cardiac Death*, article origin unknown, Apr. 21, 1999, two pages.

*The 12–Lead ECG and the Extent of Myocardium at Risk of Acute Infarction: Anatomic Relationships Among Coronary, Pukinje, and Myocardial Anatomy*, date unknown, pp. 16–30.

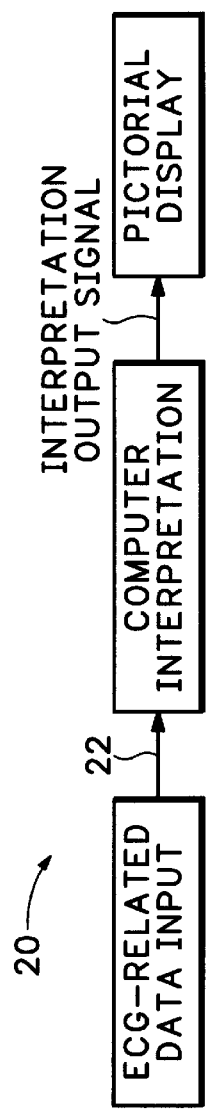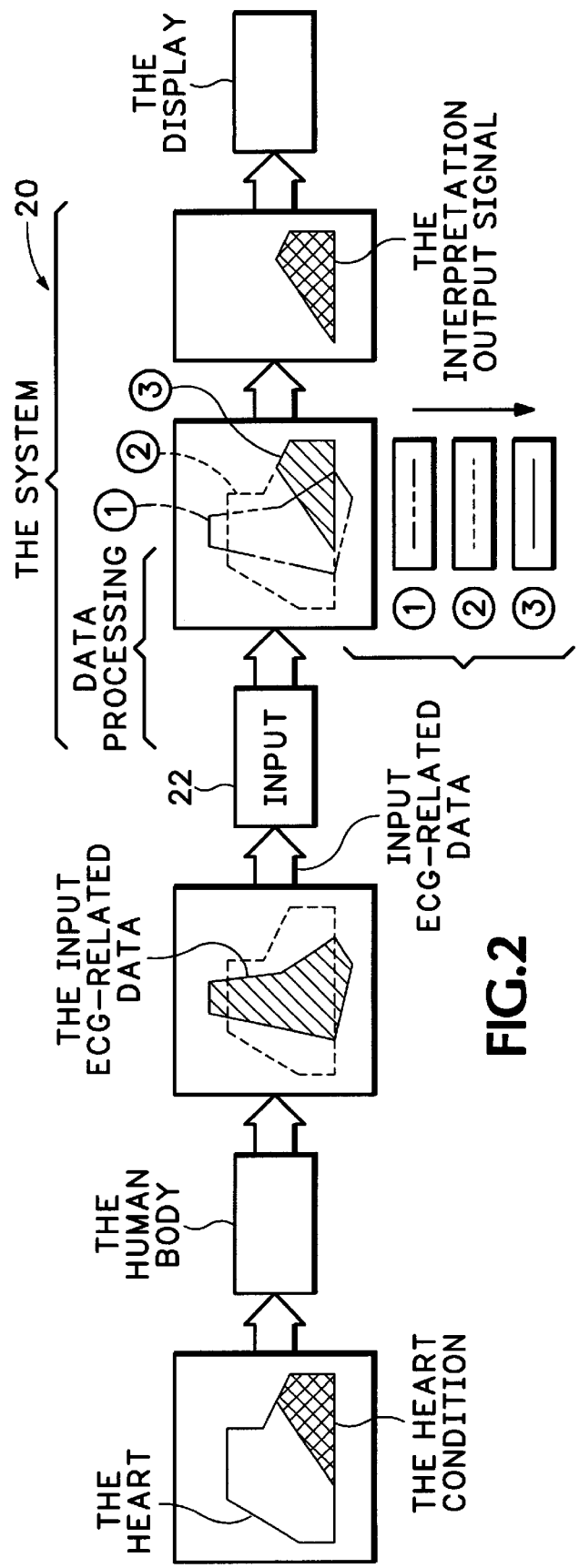

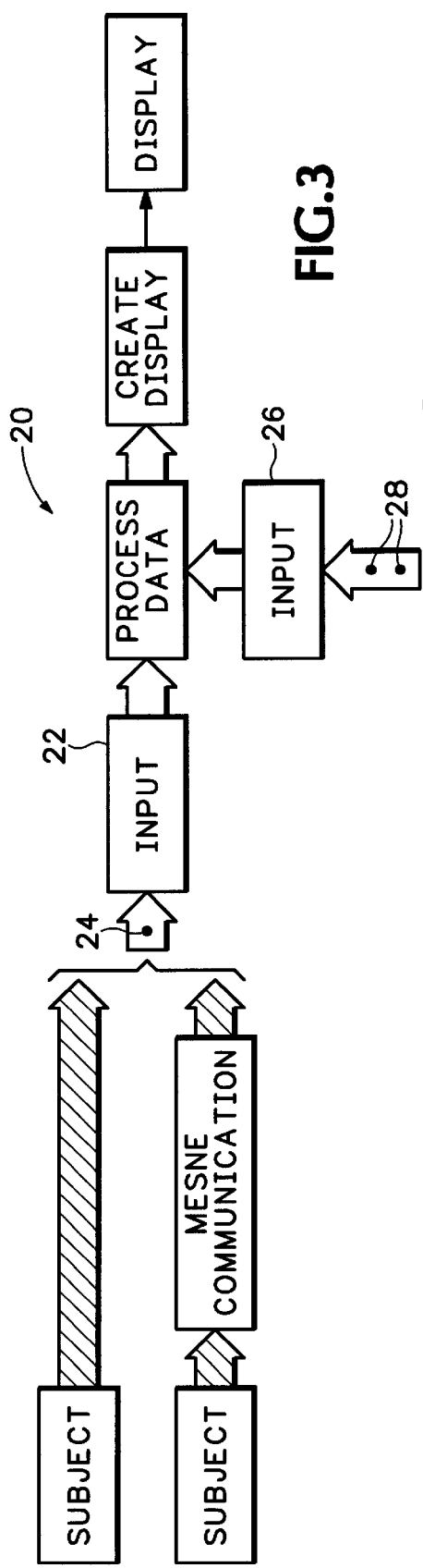
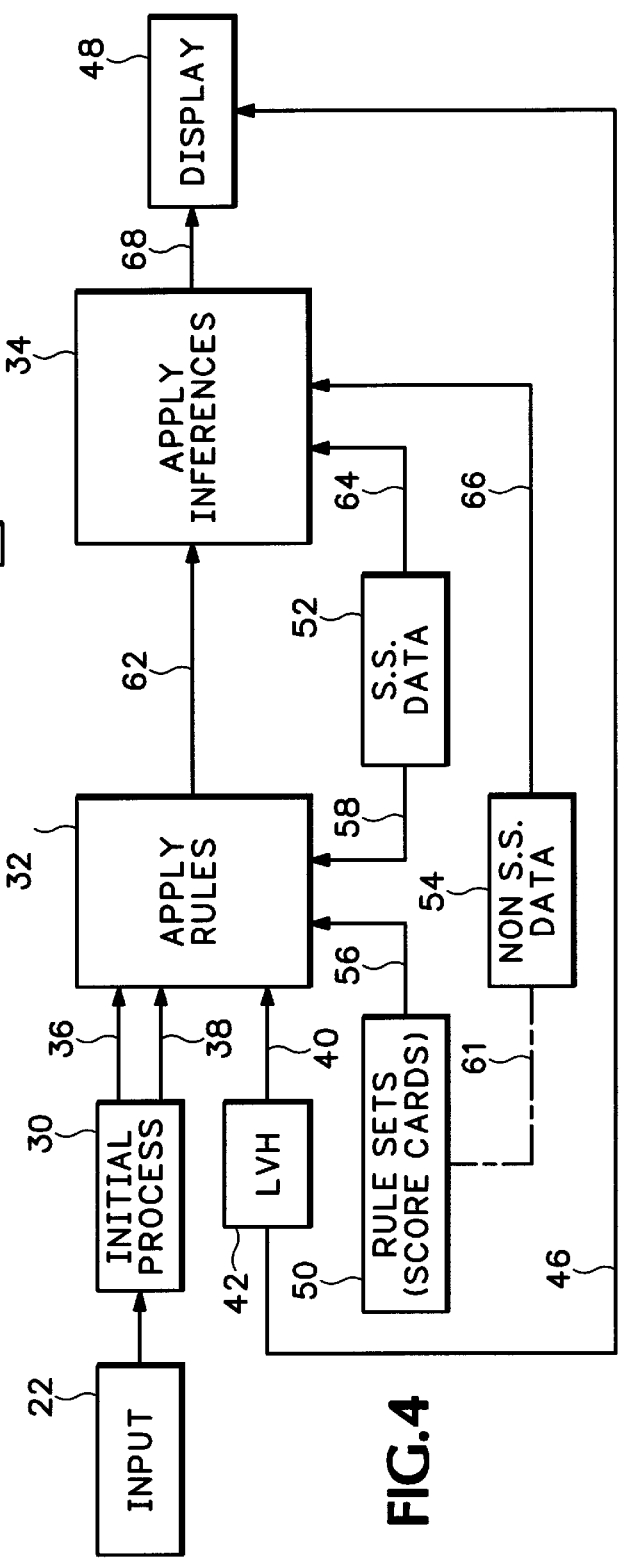
FIG.3
FIG.4

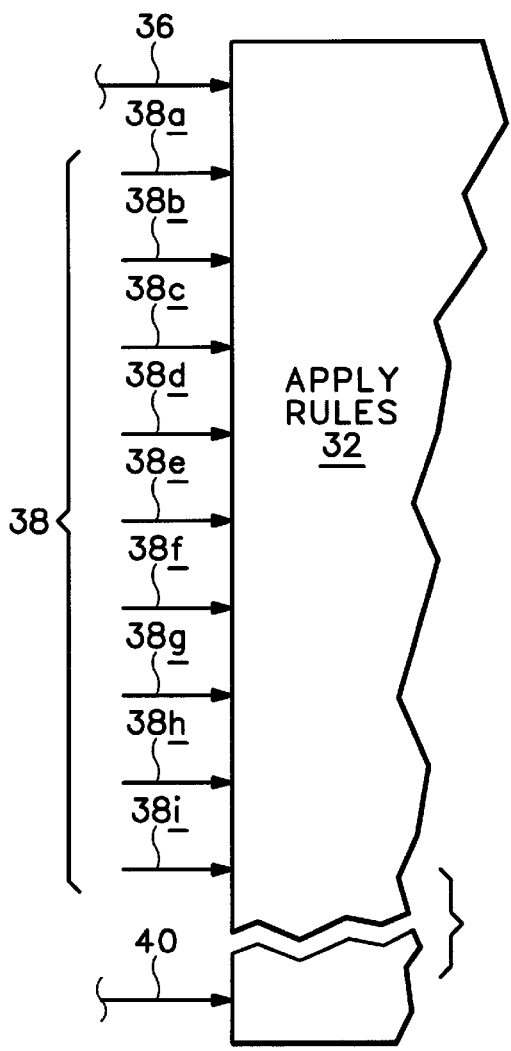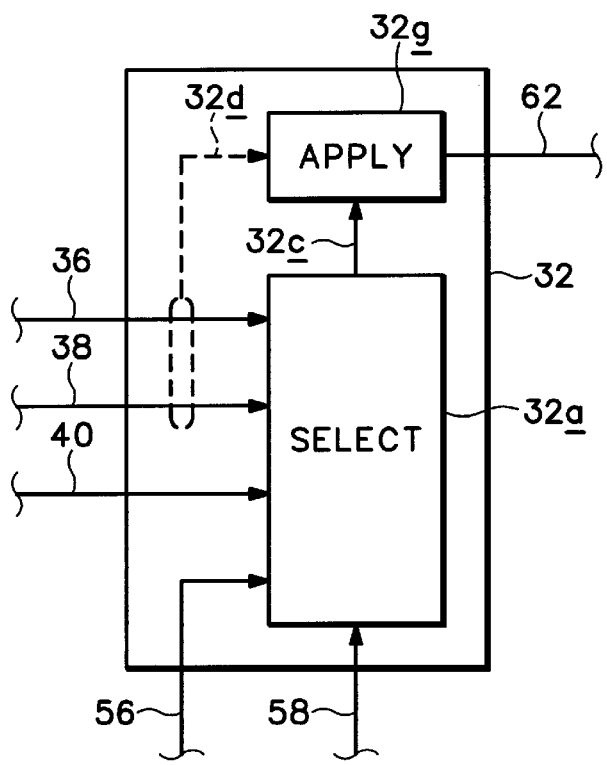
FIG.5A
FIG.5B

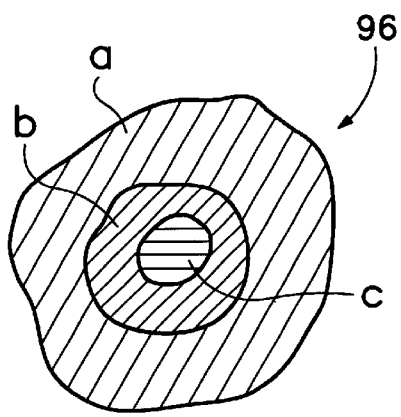 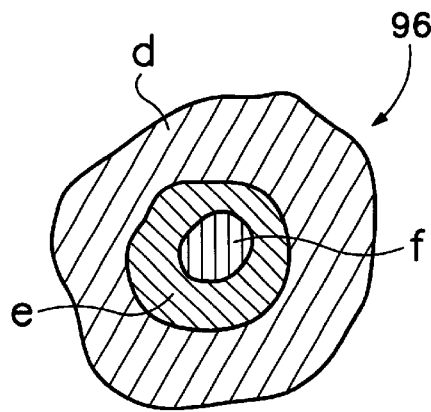
FIG.14A  FIG.14B
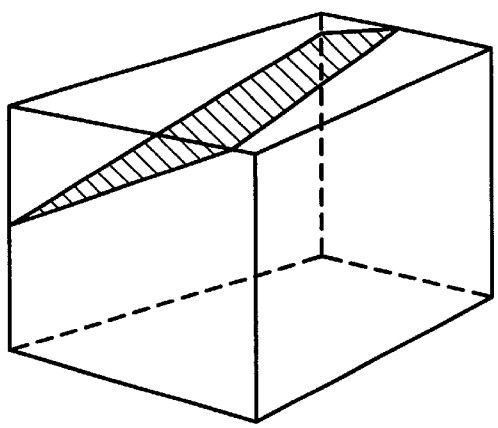 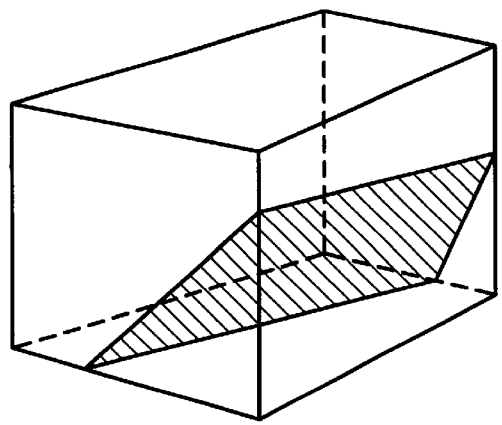
FIG.15A  FIG.15B

PICTORIAL-DISPLAY ELECTROCARDIOGRAPHIC INTERPRETATION SYSTEM AND METHOD

CROSS-REFERENCE TO RELATED APPLICATION(S)

This application claims priority to Provisional Application Ser. No. 60/100,736 filed on Sep. 17, 1998 entitled "Method and System for Acquiring and Presenting Visual Images Related to Physiologic Anatomic Conditions."

BACKGROUND AND SUMMARY OF THE INVENTION

This invention, in one of its aspects (the preferred aspect), relates to a medical-assistant system and method utilizing digital computer processing for interpreting a specific subject's electrocardiographic (ECG) waveforms. In particular, and with regard to this aspect, it relates to such a system and method which, after performing a computer-implemented interpretation of input ECG data, ultimately creates a pictorial, representational output display of the heart marked, inter alia, with distinctive visual elements (markers) that show, with a very high degree of configurational and other accuracy, the natures, presences, sizes, locations, and other aspects, of certain selected heart conditions. These conditions, also referred to herein as features (or regions), include (without limitations) any one (or more) of the following: (a) myocardial infarcts (old, acute and subacute); (b) ventricular mass; (c) all forms of hypertrophy; (d) localized ischemia; (e) ectopic foci; and (f) any other heart condition of interest (such as activation wavefront information) which is detectable in ECG data. The resultant, desired pictorial output display (static, and/or with motion) can be presented (1) on a screen such as a computer monitor or a projection screen, (2) as a spatially floating real image, (3) on a printed sheet of material, or (4) in any other suitable manner.

Another aspect of the invention involves a medical-assistant system and method including an input zone structure adapted to receive an already prepared computer interpretation signal containing heart-condition information like that just mentioned. This input zone structure is coupled to what is called herein a pictorial display subsystem which uses the already prepared signal to produce the desired pictorial output display.

In operation, the system of the invention in its preferred aspect is furnished with an input collection (or stream) of subject-specific ECG-related data. This data may come in the form of ECG wave data derived directly and "currently" from a particular subject, or in the form of ECG data earlier gathered from a selected subject and made available from a suitable pre-collection database, or in any other appropriate fashion. The specific ECG data provided as an input to the system may either be substantially pure and unprocessed en route to the system, or it may be in a form which has, in some way, been pre-processed in accordance with various selectable and conventionally understandable ECG-wave processing techniques. For example, arriving input ECG information may have been preprocessed through a temporal filter to remove certain electrical interference signals; it may have been preprocessed to determine interval measurements of P, QRS, and T wave offsets; it may have been preprocessed to determine certain wave amplitudes; etc. Additionally, this data may include components that result from the presence and operation of a pacemaker.

In the preferred form of the invention, the proposed system includes: (a) a first data input structure adapted to receive, from a selected subject, ECG-related data in one of the forms just mentioned above; (b) a second data input structure adapted to receive, selectively, one or two categories of physiological/anatomical data, as well as a collection of predetermined rules (also referred to as rules and criteria, as rule sets and criteria sets, and as score cards) designed to be used in the interpretation process; and (c) a digital computer (data-processing structure) which conducts the intended interpretation. The computer just mentioned is also referred to herein as being a part of an interpretation system, and it can take any one of a number of different specific forms, including a form wherein its structure is distributed in and throughout the system. The predetermined rules and criteria are also referred to herein as being expressions of selected interpretation protocols. The two categories of physiological/anatomical data include (1) general, non-subject-specific, heart-related physiological reference data preacquired from a large population of people and appropriately organized in accordance with typical heart-normalcy or heart-abnormalcy and other factors (identified more specifically below), and (2) a collection of subject-specific physiological/anatomical data (including medical history data), such as (but not limited to) subject height, weight, sex, race, torso configuration, prescription drug-use history, heart size, heart location and heart orientation. Such "heart" information is typically inferred, at least in part, from external, anatomic measurements. The input ECG-related data is also called a first collection of data, and the other data mentioned is also called, collectively, a second collection of data. The mentioned subject-specific collection of data can be input the system at the time of inputting a particular subject's ECG-related data, or it can be made appropriately available from, for example, a pre-created subject data base.

Also taken into account in the preferred practice of the invention (though not in all approaches toward employment of the invention) is information (such as presence, and level of severity (LV mass)) relating to all forms of hypertrophy, such as left and right ventricular hypertrophy. In the description which is given below of a preferred form of the invention, that form is presented herein, just for illustration purposes, in the context of receiving and employing information regarding left ventricular hypertrophy (LVH) and LV mass.

Preferably included in the organized, non-subject-specific, general-population reference collection of such data is information regarding gender, age, race, height, weight, body build, transverse chest measurements, and related information concerning expected major variances attributable to differences in typical male and female torso anatomy. Also preferably included in such a library of general-population data, is additional information describing typical normal conduction, ventricular and other hypertrophies, typical anterior, inferior and posterior infarcts of all sizes, and regional sub-endocardial, mural and transmural injury-ischemia. Further, this collection of general-population data preferably covers a range of subjects which would include, by physiological and anatomical characteristics, each specific singular type of subject whose ECG data might be expected to be interpreted by the system and method of this invention.

As will be more fully described below, according to the preferred manner of practicing the present invention, the implemented interpretation process involves the use of both subject-specific physiological/anatomical data, and in relation thereto, selected data contained in the general-population physiological/anatomical database. This selected data is that which is most closely associated with a subject whose physical characteristics substantially match (or are as close as possible to) those of the specific subject whose ECG data is being examined.

As will be discussed below, the present invention also embraces modifications which relate, inter alia, to (1) the use or non-use of inference interpretation following rules application, (2) to the use or non-use of one or both categories of the above-mentioned physiological/anatomical data, and (3) to the use or non-use of hypertrophy information. Not all of these recognized modifications are specifically represented in the drawings presented herein. Rather, some of them are introduced and discussed only in text which describes them in relation to easily pictured variations of particular drawing figures which are specifically presented herein.

The central preferred heart-related method implemented by the system of the present invention can be described as including the steps of: (a) accessing, acquiring or receiving an input collection of subject-specific ECG-related data sourced ultimately from a specific living subject; (b) computer-processing (analyzing) that data to develop an interpretation (interpretation analysis) which relates to detection and characterization of certain selected heart conditions; and (c) generating, or effecting, a pictorial, representational output display of the subject's heart (also called herein a heart-representational visual display), with that display including, inter alia, visual markers specifically and inferentially associated with the found and characterized selected heart condition or conditions. This pictorial output display is created in response to what is referred to herein as a visual-pictorial-display-enabling interpretation output signal—a final output signal which results from the mentioned computer processing.

Generally speaking, the application of rules and criteria to ECG data for the purposes of interpreting pathological conditions is well known in the art. It is also known that physiological conditions such as race, age and sex of a subject are important to take into account when applying the rules and criteria. However, significantly lacking in the prior art is knowledge relating to the use of rules and criteria in the presence of ECG "confounding" conditions, such as left ventricular hypertrophy, right bundle branch block, left ventricular fascicular block, and intraventricular conduction block. These and other confounding conditions, such as left bundle branch block and pacing due to a pacemaker, currently appear, according to conventional thinking, to prevent the use of rules and criteria in a computerized ECG interpretative system.

With our new system and method, we offer a way through and beyond this dilemma.

The method and system proposed by this invention can be used either in a current-time, or in a later-time (time-displaced or time-sequential), kind of interpretive activity. They can derive ECG input information in a host of different ways (discussed more fully below). Utilizing direct, rule-based computer analysis of ECG wave data, including the applications of selected rules and criteria for interpretation, and the employment of selected inferences, they can quickly produce a highly informative visual, pictorial output display of the type generally mentioned above. In the output display, they can offer different kinds of pictorial points of view. Further, they afford the opportunity to make rapid, visual, time-separated comparisons which can clearly show changes in a selected heart condition.

In addition to what has been stated above about our new system and methodology, this system and methodology is capable of furnishing, in pictorial display form, (a) a predictive output display which forecasts changes in heart condition that might be expected at different later points in time, and (b) a cine-loop type motion display which shows how a detected condition affects heart pulsation. For example, it is possible to use the system and method of this invention in a serial-comparison mode of operation, wherein the kinds of activities that are predictive precursors to the onset of an acute myocardial infarct can be detected, pictured and relied upon to initiate preemptive medical intervention. Describing generally how such predictive behavior can take place using the present invention, the following representative actions are illustrative: (a) on the basis of one ECG interpretation procedure, producing a pictorial display of the heart, marked with a selected heart condition existing at time $T_1$; (b) on the basis of another, later ECG interpretation procedure, producing another pictorial display of the heart, marked with a related selected heart condition existing at time $T_2$; (c) applying an appropriate future-condition-predictive knowledge database associated with the differences existing in the displays of conditions at times $T_1$ and $T_2$; and (d) offering a predictive interpretation as an outcome of action (c).

Another unique capability of the system and method of this invention is that it can be employed, on the basis of a given interpretation which it performs, to produce a display (relative to that interpretation) that pictures electrical activation wavefronts associated with the heart condition found in the interpretation. Such wavefronts can be presented in various visual ways, such as in distinctive bands of color, which represent time and spatial displacement in the heart.

Augmenting and reinforcing what was just said above about the output display, this display can be presented in the form either of a static or of a motion display. It can be shown in the form of a floating, real-image display. And, it can be furnished in a manner which permits elaborate, real-time user manipulation (for example, selective rotation). As was stated earlier, of course, other manners of display are possible. For example a resulting pictorial output display could be transmitted to a remote location, as, for example, by transmission over the Internet.

If desired, the final interpretation output information can further include (along with a pictorial display) any one or more of: (a) a written report; (b) an appropriate alarm signal (as, for example, in a typical patient-monitoring mode of activity); (c) an action control signal, such as a signal which causes the automatic administering of a medication; and (d) other things.

While various different representational visual display formats can be employed to suit different applications, one format which we believe will be considered to be very effective in many instances, and which is specifically illustrated herein, is the screen-borne (or printed) format of a map-like Mercator projection of the epicardial (outer) surface of the left ventricle (accompanied, if desired, by a single-side view of the right ventricle). Specifically what is shown in one of the drawing figures herein is a view which includes, in addition to the just-mentioned, single-side right ventricle view, such a Mercator projection, wherein the left ventricle is displayed in four quadrants as described by Ideker, each quadrant being divided into basal, middle and apical segments. For ease of identification and orientation, these segments are conventionally numbered 1–12, inclusive. In this generally representational display, and specifically in the left-ventricle part of the display, there is an image of a single, moderate-size infarct which extends over two quadrants and several segments of the left-ventricle. The displayed infarct takes the form of a patterned, or color-highlighted, shape. This shape generally expresses visually the location, size, configuration and disposition of the infarct. Such patterning or color-highlighting, which can take any one (or more) of a number different forms, is very useful in identifying and detailing subtle differentiating characteristics that are present within a detected condition, such as within an infarct. In the particular representative displays (and there are several) presented herein, such patterning/highlighting is employed to reveal infarct density information.

Representative displays of other conditions, such as displays regarding ectopic foci and ischemia, are not specifically pictured in the drawings. Rather, these other kinds of displays are described in text which relates them to the particular infarct displays that are shown in the drawings.

Other advantages which are offered by the present invention will become more fully apparent as the system and method descriptions which now follow are read in conjunction with the accompanying drawings.

DESCRIPTION OF THE DRAWINGS

FIG. 1 is a block diagram that illustrates generally in preferred form both the system and the method of the present invention.

FIG. 2 is a block/schematic diagram which, in a kind of story-telling way, describes the performance, the logic and the architecture of the invention pictured in FIG. 1.

FIG. 3 is a block diagram which, somewhat more elaborately (in relation to FIGS. 1 and 2), expresses the make up of the system and the method of this invention.

FIG. 4 is a detailed block diagram which fully illustrates the internal operating structures and procedures of the invention shown in FIGS. 1 and 2.

FIG. 5A is an enlarged, fragmentary block diagram which shows details involving the input of information to a block labeled APPLY RULES in FIG. 4.

FIG. 5B is an enlarged, fragmentary block diagram showing details regarding the content and behavior of the APPLY RULES block in FIGS. 4 and 5A.

FIGS. 14A, 14B picture, through the use of several different forms of shading, two time-displaced output displays of a selected heart condition which has certain plural internal features that have changed over time FIGS. 15A, 15B employ two images of the intersection between a plane and a simple cube to illustrate graphically the capability of the method and system of this invention to present the same detected selected heart condition from plural, different points of view.

DETAILED DESCRIPTION OF, AND BEST MODE FOR CARRYING OUT, THE INVENTION

Figure 5C:
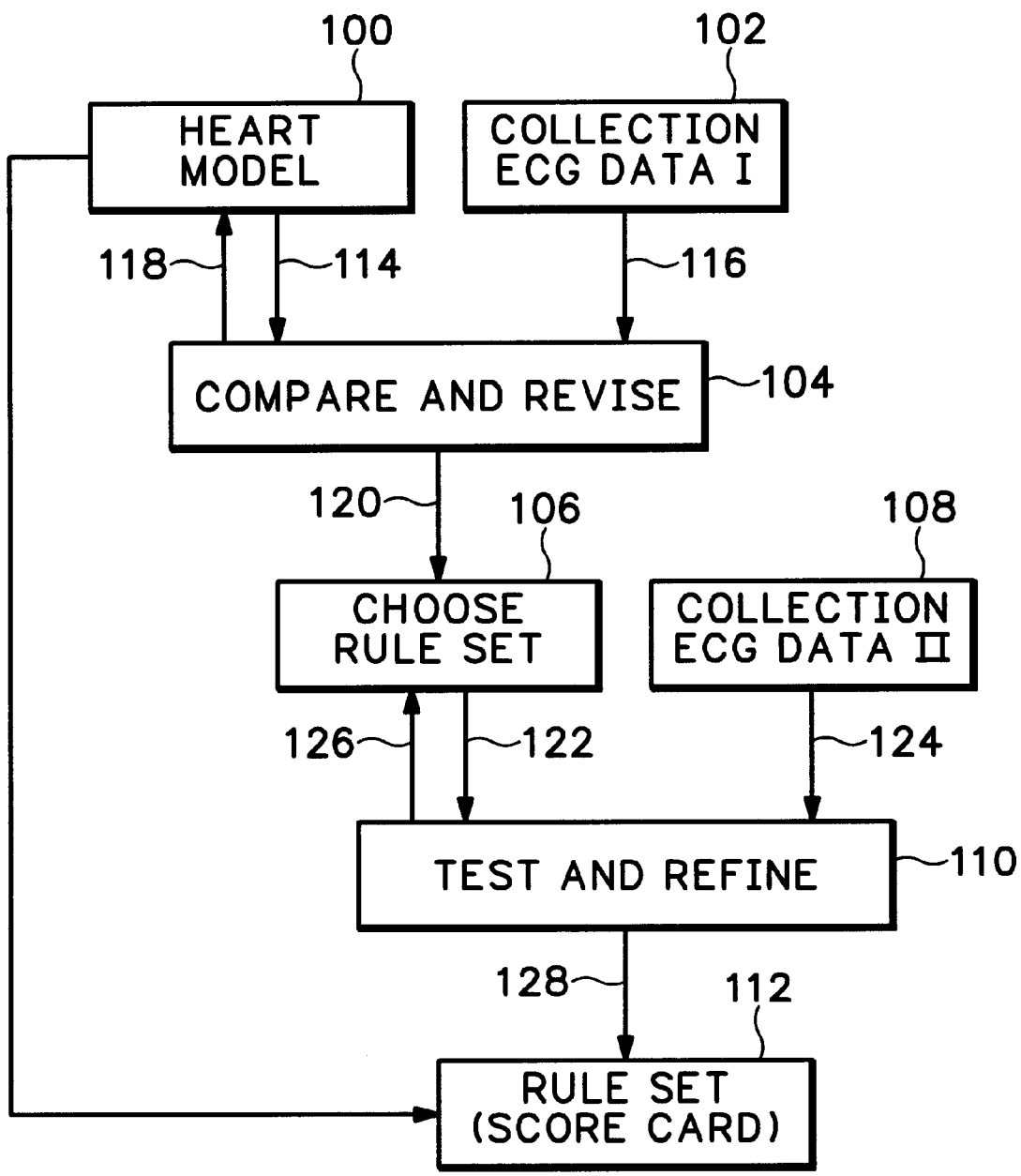
FIG. 5C is a block/schematic diagram describing a way of creating ECG interpretation rules that reside in a block labeled RULE SETS (SCORE CARDS) in FIG. 4.

Turning attention now to the drawings, and referring first to FIG. 1, here there is shown, in rectilinear block form at 20, and in a broad-brush manner, the overall system and method of the present invention. As is illustrated in this figure, subject-specific ECG-related data is furnished as an input. This data is processed by structure including a digital computer to arrive at an interpretation (an interpretation output signal) which is capable of driving a pictorial output display structure. Specifically, this output signal (also referred to as a visual-pictorial-display-enabling signal) causes such a pictorial display structure to create a display which is like that shown, for example, in FIG. 6A.

The ECG input data can be acquired from a subject, and delivered to system 20 as input information, in any suitable conventional manner. It can arrive and be received at the ECG input to the system via any appropriate and conventional data-transmission medium. It can arrive either as unmodified ECG wave data (typically, in the form of plural waveforms), or in a modified form which results from some category of conventional or otherwise easily understandable pre-processing. It can contain pacemaker-introduced components. It can be delivered in a substantially real-time fashion, as, for example, from leads in a conventional sixteen-lead or twelve-lead procedure; or, it can be delivered from any suitable memory database which has previously been loaded with appropriate ECG data. Worthy of note here is that, if desired, ECG-related input data could also take the form of ECG-related measurements.

In general terms, the form of such data delivery does not affect the basic structure and operation of the invention.

For the sake of illustration and description herein, we will assume that the presentation of input ECG data to system 20 occurs in a generally current-time fashion, and takes the form of sixteen-lead data that has been digitized, but otherwise unmodified. We will assume further that this data is presented to the system with a faithful digital rendering of each and every one of the generally expected sixteen-lead, plural-wave components derived through a well-known process called ensemble averaging from a large plurality of conventionally gathered and selected ECG waveforms. This input ECG data includes the appropriate waveforms that will carry with them electrical information relating to the various selected heart conditions which the present invention is intended to observe. It may also include pacemaker-generated characteristics. Such data, as those skilled in the art readily know, includes the usually expected information arrayed in four distinct, broadly-described categories including signal amplitude, signal timing (in relation to the onset of a cardiac cycle), signal directionality (in relation to where on the subject's body input lead conductors are placed), and inter-wave relational data involving any one or more of specific correlations that exist between two or more of the wave components of the ECG input data.

As an important aside comment at this point, the choice made herein to illustrate our invention in relation to preferred sixteen-lead input data is not a limiting consideration. Other well-recognized lead-set sizes could be used if desired. For example, all statements made herein about how the system and method of this invention perform can, and do, apply equally well to the receipt of conventional twelve-lead data. The illustrative and preferred sixteen-lead format is chosen because of the relatively fuller information content which it carries. The system and method of the invention can also be used, if desired, in relation to smaller (less than twelve) lead sets.

FIG. 2 presents a schematic way of viewing the operation of the preferred system and method of the invention. Progressing from left to right through this figure, the left-hand block contains an irregular, seven-sided geometric figure which is intended to symbolize the "electrical character" of the heart. This character is that which would be exactly contained in ECG waveforms if such were collected directly from electrical contact made with the heart surface per se. Within this geometric form, there is pictured a four-sided, cross-hatched region. This region symbolizes the particular and unique electrical characteristics, or specific, original electrical "signature", of a selected heart condition (such as an old infarct) which is present in the heart. This signature is one that would be expected to be confirmedly present and fully contained in direct-contact, heart-surface ECG waveforms.

The block immediately to the right of the one just discussed represents the human body, and it is so labeled. Very specifically, this block represents, very simplistically, the several different regions of the body which lie between the surface of the heart and the surface of the skin. In particular, and thinking of the body as being a volume conductor, this block symbolizes the volume conduction paths in the body that lie between the heart and the skin at the locations where a conventional sixteen-lead conductor set would be connected. As is well recognized, these conduction paths act as filters of the electrical information which is communicated to these skin locations from the heart. Accordingly, it is body-filtered ECG information that becomes the usually accessible source of subject-specific ECG data.

As will be apparent to those skilled in the art, it is certainly possible that the "source" ECG data could come from a mix of skin-surface-derived as well as heart-surface-derived contact locations. For example, certain ECG data could come directly from an internally placed pacemaker-like device.

With such a mix of input sources, the present invention can readily be postured to deal with the different kinds and levels of relative body filtering which occurs.

The next block pictured progressing to the right in FIG. 2 contains, in dashed lines, a symbolic representation of the "electrical heart" as such would ideally appear in surface-skin-derivable ECG information were it not for the fact that the body has acted as an electrical filter. The solid-outline, six-sided, shaded form in this block is intended to picture symbolically the changed (filtered) electrical representation of the heart that appears in actual surface-received ECG information. This representation is labeled in FIG. 2 with the words THE INPUT ECG-RELATED DATA. It is this body-filtered ECG information which is what is effectively supplied as an ECG input to the system of this invention as such is now being described. The input structure, referred to also herein as a first data input structure, for this ECG data is represented by a block numbered 22. Input 22 is illustrated as an arrowhead in FIG. 1.

Accordingly, there is provided to the ECG data input of system 20, ECG-related data which arrives with an electrical character that is somewhat different from the electrical character that one would get if one were acquiring such data entirely from the surface of the heart.

This input ECG information is next subjected to preliminary digital computer processing for the purpose of leading toward the final interpretation output signal as mentioned above. The computer structure (and its operation) in system 20 are symbolized by the bracket in FIG. 2, which bracket is labeled DATA PROCESSING. The exact construction of this computer and its exact placement in the system are not features of the present invention. For example, the computer components may reside all in one location, or these components could be appropriately distributed throughout the system. Accordingly, these matters are not described herein in detail. What is important is that this computer be programmed to be capable of performing the desired ECG interpretation. Such programming can be accomplished in various well-known ways. Because of this, and because the details of a selected programming approach form no part of the present invention, we do not direct any detailed attention herein to this subject matter. We do describe below, however, the interpretation logic which is required generally in order to practice the invention, and it is this logic which determines the otherwise well understood architecture for appropriate conventional programming. Also, we describe below how rules and criteria (score cards) for interpretation can be created and applied, how inferences can be chosen and used, and how an appropriate pictorial display with markers can be generated.

As will be more fully discussed below, programming embodied in this system and in its associated method is designed to implement several stages of ECG-data examination and interpretation. One such stage involves preliminary (or pre-) processing to develop certain initial information regarding (1) sinus or ectopic focus and (2) conduction characteristics. The pre-processing activities are also referred to herein as analyzing and assessing activities. Another stage involves the subsequent application of selectable rules (all, or a portion only, of an available library of rules) for interpretation. This activity is also referred to herein as computer-correlating activity, with an outcome which is referred to as a correlation nexus. These rules are applied in an environment which involves, in addition to the outcome of pre-processing activity, relevant hypertrophy information. As was mentioned earlier, the preferred form of the invention is discussed herein specifically with reference to the use of left ventricular hypertrophy (LVH) information. A third and later stage involves the application of selectable interpretation inferences. In each of these stages, the full content of the input ECG data is present for review-access and examination.

Continuing in FIG. 2, the right-hand block under the DATA PROCESSING bracket includes three irregular geometric figures, one of which is pictured in dash-double-dot lines (labeled ①), another of which is pictured in dashed lines (labeled ②), and the third of which is pictured shaded in a border of solid lines (labeled ③). These three figures symbolize a particular interpretive behavior of the system and method of present invention. This behavior can be thought of as something which "sees through" the changed ECG signal that directly appears on the surface of a subject's skin, to "find" the correct, original electrical picture (or pictures) of the one or several selected heart condition features that are being sought. Presented below the block that contains these three figures is a vertical stack of three rectangles each containing a different one of the three different line characters which are employed to outline the three figures now being discussed. The downward pointing arrow to the right of these rectangles indicates, very generally, the "order" of data processing which now (in the operation of system 20) leads to generation of the desired final interpretation output signal.

Figure ① represents the electrical character of the heart as is contained in the previously discussed input ECG-related data. Figure ② symbolizes the virtual re-creation substantially of the (un-body-filtered) electrical character of the heart as is pictured in the left-hand block in FIG. 2. Figure ③ symbolizes the virtual and relatively faithful recreation of substantially the original electrical signature of the mentioned infarct condition. These three (①, ②, ③) figures, and the ways that we characterize them here, are presented as analogies for envisioning the effective operational activity of system 20.

Progressing now through the remaining part of FIG. 2, such processing ends up in the generation or creation of the mentioned, desired interpretation output signal. This output signal is shown graphically in FIG. 2 in the block immediately to the right of the one containing the three (①, ②, ③) figures. The cross-hatched, four-sided, shaded graphical element here symbolizes the desired interpretation output signal—so labeled. This graphical element visually replicates the same heart-condition symbol that appears in the far-left block in FIG. 2.

Accordingly, the several block-contained geometric figures which are set forth in FIG. 2, as such has so far been described, illustrate the powerful interpretive and illustrative capability of the system and method of this invention.

The ultimately created interpretation output signal is effective to produce, with the aid of conventional visual graphics display apparatus which is represented by the block labeled THE DISPLAY, the desired pictorial output display of the heart. Specifically, the interpretation output signal that is generated results in the visual presentation of a pictorial, and generally anatomically representational, view of the heart, appropriately marked, inter alia, to illustrate, quite realistically, the found area or areas of one or more selected heart conditions.

Expressing in somewhat different terms what is shown in and with respect to the description given for FIG. 2, it is here that an important characteristic of the method and system of the present invention is fully expressed. Within the category of selected heart conditions that are examined and made viewable pictorially by the present invention, each one of these conditions can be thought of as existing as a real three-dimensional portion of the associated heart. Each of one of these things has real boundaries, a real position, a real orientation and real internal physical characteristics. Each such condition also has a fully expressive and distinctive electrical signature which makes its imprint upon, and contribution to, the electrical ECG behavior of the heart. This signature is fully and precisely contained within the electrical ECG waveforms generated during a cardiac cycle of the heart. Accordingly, such a signature is fully present, unfiltered, at the outside surface of the heart. The "condition signature" arrives in a filtered condition at the skin surface. Interpretation activity performed by the present invention essentially undoes the filtering which has occurred, and because of this, the invention effectively "gives itself" substantially accurate possession of the original condition signature.

Such a condition signature can thus be thought of as retaining, effectively, a substantially unblemished quality (not translated out of the digital data "machine" world) as it "travels" through the method and system of the invention, on the way toward emerging in the final interpretation output signal. From the moment that it is collected at a subject's skin surface, it enters and remains in the digital-data "machine" world, and this situation affords a unique and special opportunity to construct an accurate output visual picture of the source condition and its effective character in the heart.

FIG. 3 in the drawings illustrates the architecture of the preferred embodiment of the invention in somewhat fuller detail. In addition, it shows several different ways in which direct-from-subject ECG data can be provided to the system of the invention. Further, FIG. 3 furnishes a way of viewing and understanding the system and the related method which includes recognizing the presence of two different input structures that feed different categories of information into the system for processing. Among other terminology employed herein to name this system, one approach refers to it as an electronic interpretation-based display structure.

At the left side of FIG. 3 are two blocks, each labeled SUBJECT, and each having a large, attached, shaded arrow extending to the right of it. The upper block and its associated arrow represent direct-from-subject ECG data input. The lower block and its associated arrow, along with the MESNE COMMUNICATION block drawn to its right, represent an indirect system input from a subject through any appropriate communication medium. The MESNE COMMUNICATION block symbolizes such a medium. This medium can include, without limitation, a pre-acquired and stored collection of subject-specific ECG data, radio-frequency transmission to an appropriate receptor, a conventional telephone line, the Internet, and so on.

ECG data arriving at system input structure 22, via any communication route, is also referred to herein as a first collection of ECG-related data. This first collection of data is represented in FIG. 3 by the single black dot 24 pictured in the stubby arrow that touches the left side of input structure 22 in FIG. 3.

As pictured in FIG. 3, system 20 includes another (or second) data input structure 26. Through this second input structure, the system receives what is referred to herein as a second collection of data. This second collection of data is represented by the two black dots numbered 28 in the stubby arrow which touches the underside of input structure block 26. The second collection of data preferably includes a suitable library of ECG interpretation rules (organized into sets called score cards), a library (a first body) of non-subject-specific physiological/anatomical data (mentioned earlier), and a library (a second body) of subject-specific physiological/anatomical data (also mentioned earlier), and also including, if desired, subject-specific medical-history data.

Turning attention now to FIGS. 4 and 5A, FIG. 4 illustrates a full block diagram of the structure and method of the preferred form of the present invention. Included in system 20, "beyond" input structure 22, are an INITIAL PROCESS block 30, an APPLY RULES block 32, and an APPLY INFERENCES block 34. It is within these three blocks that substantially all of the interpretation work which is performed in accordance with the invention takes place in stages.

Data received by input structure 22 is fed to block 30, wherein it is processed to extract essentially two different categories of information. These two categories are made available respectively on two different outputs from block 30. These two outputs are represented by single lines 36, 38 in FIG. 4. Lines 36, 38 are merely symbolic of the presence of appropriate signal-flow connections and paths that are present in system 20. In some instances, these flow paths take the form of conventional computer bus structure which can incorporate multiple individual flow paths. Such bus structure is well understood by those skilled in the art of computer architecture.

From block 30, line 36 conveys information regarding the presence or absence of an ectopic focus finding. It also conveys the full, original ECG data received at input 22. Line 38 carries a category of output information which describes the presence or absence of a detected conduction defect. In addition, it also conveys the full, originally received ECG data. Lines 36, 38 are connected directly to appropriate inputs for APPLY RULES block 32.

Also feeding information (LVH information) into an appropriate input for the APPLY RULES block, via a line designated 40, is a block 42 labeled LVH. Output LVH information from block 40 is also supplied on a line 46 directly to the graphics display structure which is pictured by a block 48 on the right side of FIG. 4.

Shown connected for feeding several categories of additional data to APPLY RULES block 32 are a RULE SETS (SCORE CARDS) block 50, and a subject-specific data block 52, labeled S.S. DATA. Connecting block 50 to block 32 is a line 56; and connecting block 52 to block 32 is a line 58. The dash-dot line which is shown at 61 in FIG. 4 as a line interconnecting blocks 50 and 54, symbolizes the capability, in the system and method of this invention, to respond to appropriate "instiuctions" conveyed from the "outside world" to modify the information contained in block 50. This capability will be more fully discussed shortly.

Three input connections are shown in FIG. 4 for APPLY INFERENCES block 34. These three connections are represented by (1) a line 62 which extends from the output side of APPLY RULES block 32 to an input for block 34, (2) a line 64 which extends from block 52 to an input for block 34, and (3) a line 66 which extends from block 54 to block 34.

Line 62 carries what is called herein a pre-inference interpretation output signal. Lines 56, 58, 64 and 66 collectively make up previously-mentioned second data input structure 26.

The final operative connection to be described in conjunction with what is shown in FIG. 4 is represented by a line 68 that extends from the output side of APPLY INFERENCES block 34 to an input side of DISPLAY block 48. Line 68 carries the previously mentioned final interpretation output signal, which output signal can be thought of as being a post-inference output signal.

Lines 62, 68 are also referred to herein independently as input zone structures, and display 48 is also referred to as a pictorial display subsystem. These reference characterizations relate to the earlier mentioned other "aspect" of the invention. This other aspect focuses attention on a system and method that involve reception of an already computer-prepared interpretation output signal at an input zone structure, and the coupling of such a received prepared signal to a pictorial display subsystem.

Where this "other aspect" view of the invention involves the receipt of pre-inference interpretation data, line 62 is viewable as the input zone structure, and display 48 as the pictorial display subsystem. In this form of the invention, line 62 in FIG. 4 should be seen as being directly coupled to display 48 at the location where line 68 is now pictured in this figure. The entire invention (system and method) in this case then reduces to the very simple two-element block diagram.

On the other hand, where the "other aspect" view of the invention involves the receipt of post-inference interpretation data, line 68 is viewable as the input zone structure, and display 48 as the pictorial display subsystem. Here also the entire invention reduces to another two-element block diagram.

Turning now to FIG. 5A as such relates to FIG. 4, within INITIAL PROCESS block 30 (shown only in FIG. 4), certain preliminary, first-stage computer investigations and interpretations of input ECG data are performed. Very specifically, within this block the input ECG data is examined first to determine whether there is or is not an ectopic focus site represented in the input ECG waveforms. The nature of such an inquiry is well known to those skilled in the art, and accordingly, is not described in any detail herein. If an ectopic focus site is in fact detected, a declaration confirming that condition is sent over line 36 to APPLY RULES block 32. What happens to this information within block 32 will be explained shortly.

If an ectopic focus site is detected, then the only information which is supplied from block 30 is that which has just been described as an indication on line 36 that a localized ectopic focus site has indeed been found. No output information flows on line 38.

If within block 30 an ectopic focus site is not found, then no information is conveyed on line 36, and the only "found-condition" information which makes its way through and beyond the INITIAL PROCESS block appears, if at all, on line 38. Very specifically, line 38, which is appropriately configured in any conventional manner to act as if it were nine independent communication "sub-lines", conveys information (to block 32) regarding any one of nine different categories of heart-conduction defects which are looked for in block 30. These nine categories of conduction-defect information can be visualized as being associated, on a one-to-one basis, with nine different sub-lines that make up line 38. These sub-lines are illustrated in FIG. 5A at 38$a$, 38$b$, 38$c$, 38$d$, 38$e$, 38$f$, 38$g$, 38$h$, 38$i$. With respect to the mentioned nine different categories of conduction-defect information, the following numbered listing describes these categories as such are associated with the just identified nine sub-lines.

1. Sub-line 38$a$: a declaration that QRST conduction is normal.

2. Sub-line 38*b*: a declaration that QRST conduction is abnormal, that there is a right bundle branch block, and that left ventricular activation is normal.
3. Sub-line 38*c*: a declaration that QRST conduction is abnormal, that there is no right bundle branch block, and that there is a superior fascicular block.
4. Sub-line 38*d*: a declaration that QRST conduction is abnormal, that there is a right bundle branch block, that left ventricular activation is abnormal, and that there is a superior fascicular block.
5. Sub-line 38*e*: a declaration that QRST conduction is abnormal, that there is no right bundle branch block, that there is no superior fascicular block, and that there is an inferior fascicular block.
6. Sub-line 38*f*: a declaration that QRST conduction is abnormal, that there is a right bundle branch block, that left ventricular activation is abnormal, that there is no superior fascicular block, and that there is an inferior fascicular block.
7. Sub-line 38*g*: a declaration that QRST conduction is abnormal, that there is no right bundle branch block, that there is no superior fascicular block, that there is no inferior fascicular block, and that there is a complete left bundle branch block.
8. Sub-line 38*h*: a declaration that QRST conduction is abnormal, that there is a right bundle branch block, that left ventricular activation is abnormal, that there is no superior fascicular block, that there is no inferior fascicular block, and that there is a left nonspecific intraventricular conduction defect.
9. Sub-line 38*i*: a declaration that QRST conduction is abnormal, that there is no right bundle branch block, that there is no superior fascicular block, that there is no inferior fascicular block, that there is no complete left bundle branch block, and that there is some form of nonspecific intraventricular conduction defect.

These respective, individual declarations about conduction-defect conditions will only exist as mutually exclusive declarations, and only if there is no detected ectopic focus. As a consequence, if there is a detected conduction defect, a statement about it will be present on only one of sub-lines 38*a*–38*i*, inclusive. Any one of these nine sub-lines which conveys declaration information to APPLY RULES block 32, also conveys the full, originally received ECG input data.

Within INITIAL PROCESS block 30, the question relating to whether there is or is not an ectopic focus is probed before any question is asked about conduction conditions. With regard to ectopic focus and the asking of conduction questions, two preliminary and well understood questions are asked. The first of these two questions asks whether the P wave component in the ECG data is responsible for driving the QRST wave components of that data. If the answer is yes, there is no ectopic focus site, and the mentioned conduction characteristics are explored. If the answer is no, no conduction exploration takes place until the second-mentioned ectopic focus question is asked, and is answered in a certain manner. This second question asks whether any ventricular rhythm is detected. If the answer is yes, then no conduction examination takes place, and an ectopic focus is deemed to be present. If the answer is no, then a determination has been made that there is no localized ectopic focus, and a conduction-characteristic review thereafter takes place.

Those skilled in the art will recognize that the above-stated initial processing questions (regarding ectopic focus and conduction) are conventional interrogative questions that are routinely posed by available ECG equipment. Looking at this situation from another point of view, it is correct to state that, within the environment of currently conventionally available ECG equipment, those skilled in the art will know exactly where to go within that environment to collect the above-mentioned categories of ectopic focus and conduction declaration information. Because of this, the requisite structure that needs to be included in the system of the invention to ask these questions can be designed directly from the use of conventional ECG art. The precise styles and orders of asking these various questions are freely matters of choice, are well within the skills levels of those skilled in the art, and do not form any part of the present invention.

Accordingly, the above discussion fully describes to persons skilled in the relevant art the required operative content and functionality of INITIAL PROCESS block 30.

As is apparent from the discussion offered so far regarding the preferred form of the invention as pictured in FIG. 4, LVH information, and specifically such information which describes the presence of LVH, and an indication of degree and/or severity (so-called LV mass), is furnished both to APPLY RULES block 32, and to display 48. This information is gathered in any appropriate conventional manner, such as via the procedure known as echo cardiography.

Turning attention now to previously-mentioned blocks 50, 52, 54 in FIG. 4, and beginning with block 50, this block represents a database library of selected ECG waveform interpretation rule sets, also called score cards. These rule sets, whose specific characters, contents and collective capability for establishing detection resolution are matters of designer and user choice, are applied in the environment of APPLY RULES block 32 to support the next phase (or stage) of ECG data interpretation. Such rule sets fundamentally describe how to look at different specific data components that are fed into block 32, and in particular, how to look at these components for the purpose of carefully and accurately characterizing the natures, locations, sizes, configurations, orientations, internal characters and other matters regarding selected, detected heart conditions. In the referred system embodiment now being described, these rule sets act in an interpretation environment (within block 32) which also includes subject-specific physiological/anatomical and medical-history data furnished from block 52, and additionally, whatever information is supplied from blocks 30, 42.

Looking now at FIGS. 4, 5A, 5B and 5C together, included structurally and functionally within APPLY RULES block 32 are two sub-blocks 32*a*, 32*b*. Sub-block 32*a* is labeled SELECT, and sub-block 32*b*, APPLY. Previously-mentioned lines 36, 38, 40, 56 couple directly to the left side of SELECT sub-block 32*a* in FIG. 5B. Line 56 couples to the underside of SELECT sub-block 32*a*. Sub-block 32*a* couples information into APPLY sub-block 32*b* as indicated by line 32*c* in FIG. 5B. Derived from any one or more of lines 36, 38 (its sub-lines) within APPLY RULES block 32 is the full originally received ECG input data, which data is furnished to APPLY sub-block 32*b* as indicated by the dashed line 32*d* within block 32. The output side of APPLY sub-block 32*b* couples with previously-mentioned line 62.

Before describing the respective operations of sub-blocks 32*a*, 32*b*, let us first discuss the characters and inputting of information from blocks 50, 52. We begin by turning attention first specifically to FIG. 5C. This figure contains a block/flow schematic diagram which describes how the collection of rule sets (score cards) that are present in block 50 may be created. One preliminary matter which should be noted is that reference below to blocks and lines in FIG. 5C, can be read to include, where appropriate, human (cardiologist) action and decision-making. For example, references to the coupling and supplying of information, and to the acts of choosing and decision-making, will in many instances best be performed by a blend of actions and decision-rendering utilizing both a computer and a trained cardiologist.

Pictured in FIG. 5C are seven blocks 100 (HEART MODEL), 102 (COLLECTION ECG DATA I), 104 (COMPARE AND REVISE), 106 (CHOOSE RULE SET), 108 (COLLECTION ECG DATA II), 110 (TEST AND REFINE), and 112 (RULE SET (SCORE CARD)). Via lines 114, 116 information is fed to block 104 from blocks 100, 102, respectively. Via a line 118, information is coupled from block 104 into block 100. Through a line 120, information is conveyed from block 104 to block 106. Lines 122, 124 couple information from blocks 106, 108, respectively to block 110. From block 110, information is conveyed to block 106 via a line 126, and to block 112 via a line 128.

As was mentioned just above, what is shown in FIG. 5C illustrates a way of generating the various rule sets that are contained within block 50 (FIG. 4). The rule creation process is now described in relation to creating a single rule set (score card), and is as follows.

In the structure and practice of our invention as it is now being described, a single dedicated and specially focused rule set (criteria set, score card) is provided in block 50 for each and every specific, nominal heart condition which is contemplated for detection and picturing in accordance with the invention. To bridge the differences that exist between closely proximate rule sets, these sets are preferably endowed respectively with appropriate "tolerance" ranges of applicability so that heart conditions which do not exactly "match" any given rule set will be "deemed" to be covered by a specific, most closely matching rule set.

The creation of each individual rule set, or score card (block 112 in FIG. 5C) is based upon a specific pre-selection and knowledge-based characterization of an assumed-to-be-correct, related "heart model" (block 100 in FIG. 5C). The long curved arrow in FIG. 5C symbolizes this statement. The particular selections and characterizations of heart models chosen for the generation of a given collection (or library) of rule sets is entirely dependent upon the wishes of the system designer who is specifying a particular system to be built in accordance with our invention. Thus, the number of rule sets chosen for such a library, and the respective conventional "proximities" of rule sets one to another, are completely determinable by the designer.

With respect, then, to the creation of each such chosen rule set, building thereof begins with the selection and characterization of an appropriate, assumed-to-be-accurate, related, preliminary heart model. This heart model, as well as related, changed heart models that are created during the early stages of rule-set building, generate synthetic ECG signals that replicate operations of the ventricles of the heart. The mentioned selection and characterization activities are well within the knowledge and skills prevalent in the current art of cardiointerpretation, and require no elaboration here. Thus, and for the creation of a particular rule set, an appropriate heart model selection is made, and an assumed characterization thereof is placed as a data collection in HEART MODEL block 100.

In our approach to creating practical rule sets, and for each such set, we define an appropriate heart-condition "characterization" (preliminary heart model and attributes) to include, for example: (a) the nature of a specific physiologic feature sought, such as an infarct; (b) the location and size of that feature; (c) the size, torso location, and orientation of the heart; (d) the presence of one or more "confounding" conditions in the heart, such as a right bundle branch block, a left anterior fascicular block, etc., that affects electrical conduction paths inside the heart; (e) the expected conduction pathways in the heart; and (f) the details of expected activation potentials. Further to our approach, we differentiate one heart-condition characterization from another on the basis of one or more selected difference(s), and defined "size(s)" of difference(s), in these several categories of heart attributes.

This initially chosen, "start-up" heart model is then preliminarily fine-tuned by testing it against (comparing it with) (COMPARE AND REVISE block 104) an appropriate, "real-life", heart-feature database (COLLECTION ECG DATA I, block 102) which is focused upon specific characteristics of real-life subjects' hearts that possess the initially chosen heart model. Lines 114, 116, 118 in FIG. 5C represent this activity. Appropriate changes are made in the initial block 100 model as an outcome of this comparing activity, and the resulting preliminarily "tuned" model is passed along (line 120 in FIG. 5C) to CHOOSE RULE SET block 106. This passage to block 106 stages the preliminarily tuned heart model data for use in establishing an appropriate, related rule and criteria set.

Thus, and further reviewing the preliminary part of an approach which we have used to create appropriate rule sets, the physical parameters of the heart model (block 100), which model is effectively a computer model, are thus adjusted in an iterative fashion until the synthesized ECG signals produced match, as closely as is deemed practical, ECG signals received from the database contents of block 102. An important factor here is that the database which is provided in block 102, for a particular selected heart condition, and thus for the generation of a particular refined heart model, should closely match in characteristics the unique set of factors and conditions that are being modeled in block 100. Preferably, this block 102 database needs to be as free of noise and unknown patient conditions as is possible. The degree of match that is achieved between the computer-generated ECG signals, i.e., the model heart signals, and those received from the block 102 database, will ultimately be limited by such factors. Accordingly, the ultimately determined degree of appropriate match is an expert (cardiologist) judgment call.

Once a heart model is achieved which gives acceptable results for the specific set of conditions and confounding factors, and other elements necessary to achieve the desired match between the model and the selected database in block 102, a conventional feature-extraction algorithm noting features such as amplitude, duration, etc., is applied to extract features from the synthesized ECG signals produced by the heart model. This information is effectively what is presented in FIG. 5C to block 106. In the specific practice of creating rules which we are now describing, block 106 is a trained cardiologist.

At this stage (the next creation sub-environment including blocks 106, 108, 110) in the overall procedure shown in FIG. 5C, a trained cardiologist plays the roles of: (a) selecting an initially human-defined rule set which is believed to be best suited for clearly identifying the just-established "tuned" heart model; (b) testing this initially-established rule set against a very large database (block 108) of subjects' hearts having all kinds of heart conditions, including perfectly "normal" heart conditions; (c) noting the accuracy or inaccuracy with which the initial rule set selects hearts that essentially "match" the model heart; and (d) making informed refinements iteratively in the rule set, with successive testing and evaluations, until a finally acceptable heart-condition-specific rule set is created. The finally-selected rule set is then made available to RULE SETS (SCORE CARD) block 50.

Within this rule-set creation procedure as just described, the information contained in blocks 102, 108 is substantially the same as the non-subject-specific data contained in NON S.S. DATA block 54.

This process is conducted so as to establish appropriate rule sets for all nominally chosen heart conditions which the system and method of the invention are designed to detect. Each such rule set is effectively a score card of specific questions that should be addressed to a subject's specific ECG-related input data in order to examine that data for an indication (condition signature) about whether a particular selected heart condition is present. Each rule set, or score card, is uniquely related to a particular family of non-subject-specific data, and in particular to such data which is predeterminedly linked specifically to a particular heart model and heart condition.

Having just given the above description of a way for creating appropriate interpretation rule sets, we wish to note that the system and method of this invention do not rest or rely (a) upon the presence and/or use of any specific sets of rules, (b) upon any specific approach to rules creation, or (c) upon any one manner of rules application in the interpretation process. Rather, the invention contemplates, accommodates and promotes substantial flexibility and versatility in the specific "rule sets" choices which a designer or a user of the invention can freely adopt, incorporate and use. Significantly, however, the system and method of the invention, in the preferred form or aspect now being described, do focus upon and establish a unique computer-based rules-application setting wherein full-context input ECG data, having been pre-screened to respond to a selected set of ectopic focus and conduction-defect questions, is made available, along with selected physiological/anatomical data, for a rules examination. In this setting, the specific system designer/user can freely specify both the contents of rules and rule sets, and the desired manners of their use.

A further interesting matter to mention is that system and method 20 can readily be equipped to receive certain modification input instructions that can alter, if desired, the contents of RULE SET (SCORE CARDS) block 50. To take effective advantage of this capability, an operative connection, symbolized by dash-dot line 61 in FIG. 4, is appropriately established between blocks 50, 54 to promote such a modification.

S.S. DATA block 52, in any appropriate form, such as in the form of a suitable digital memory, contains a collection of heart-related physiological/anatomical information and medical-history data which is specific to the subject whose ECG waveforms are being interpreted. This data, freely selectable in content as it is, preferably includes a range of categories of subject-specific information, such as those several categories particularly mentioned earlier herein. In system and method 20 as such are now being described, this subject-specific data is employed in the APPLY RULES block, and especially in SELECT sub-block 32a, to affect the outcome of rules applications. More will be said shortly about this area of data interpretation.

Well known in the field of electrocardiointerpretation is the fact that very similar, and sometimes almost the same, ECG waveforms can come from different subjects, and can mean very different things despite their (the waveforms') apparent likenesses. For example, two very similar ECG data sets received from two different subjects could yield two very different interpretation outcomes because of differences in one or more specific physiological/anatomical characteristic(s). The use, therefore, of both subject-specific and non-subject-specific physiological/anatomical data in the preferred implementation of this invention, and particularly in the defining of applicable rule sets and the selection thereof in sub-block 32a offers important advantages in certain situations. The use of such data helpfully focuses attention, for example, on how best to evaluate a particular subject's ECG data.

As a specific illustration of what takes place in block 32, the computer in system 20, within the environment (sub-blocks 32a 32b) of the APPLY RULES block, examines, and selects for particular attention and treatment, different components of the various input information provided to block 32. This information includes whatever (if any) data is supplied on line 36, whatever (if any) data is supplied by one of the sub-lines in line 38, and whatever (if any) LVH information is supplied on line 40. Additionally, the provided information includes rule sets from block 50, and data from block 52.

SELECT sub-block 32a directly receives whatever information is furnished on lines 36, 38, 40, as well as the relevant subject-specific data contained in block 52. With this information in hand, sub-block 32a effectively examines the data in block 50 to locate the rule set (or score card) which most closely relates to the specific data arriving on lines 36, 38, 40 in relation to the subject-specific data furnished on line 58.

With this examination successfully completed, SELECT sub-block 32a effectively feeds the correctly selected rule set to APPLY sub-block 32b. The APPLY sub-block then applies this rule set to the originally-received, system-input ECG-related data to determine what heart-condition is present, and to produce, on line 62, the pre-inference interpretation output signal previously mentioned. In system and method 20, this pre-interpretation output signal takes the form of a collection of twelve numbers each having a value in the range 0–8. Each one of these twelve numbers is associated specifically with a different one of the twelve left-ventricle sections discussed earlier. The value of the number, within the range mentioned is an indication not only whether a particular heart-condition physiology resides in that section, but also the "degree" of its presence, for example, its density.

As an illustration of a typical interpretation output situation, block 32 might determine that an infarct condition, or a plurality of infarct conditions, exists in a subject's heart. Block 32 might additionally determine that each detected infarct condition has a particular size or value (0–8).

Moving along now through the system and method as such are pictured in FIG. 4, the operating computer, on conducting such an APPLY RULES processing/interpretation, hands the interpretation result (the pre-inference interpretation output signal) to APPLY INFERENCES block 34. As we will discuss further shortly, a modified system and method having a somewhat different capability than does the system exactly pictured in FIG. 4, but nevertheless made in accordance with this invention, might be one specifically designed just to provide a pictorial output presentation based solely on such a pre-inference interpretation output signal. Such a modified form of the invention would not include APPLY INFERENCES activity.

Continuing with a description of the invention as shown in FIG. 4, the pre-inference interpretation information furnished to APPLY INFERENCES block 34 is supplied along with data drawn from blocks 52, 54. Within block 34, the computer responds to data received from the APPLY RULES block, and from the S.S. DATA and NON S.S. DATA blocks, to apply one or more inferences that further (in a third interpretation stage) characterize and interpret the information about a selected condition (or conditions) found so far in the input ECG data (the twelve numbers and values mentioned above). These inferences can, in total number, be as large or small as a particular designer/user wishes to have available for expected particular situations, and can be defined freely and flexibly to have as wide and detailed a scope as is deemed appropriate. Inferences are selected from an expert knowledge base about ECG interpretation. They can be envisioned as things which define different heart-condition profiles that are inferred from a pre-inference interpretation, such as that discussed above in relation to the pre-inference interpretation output signal generated by block 32. The exact natures of inferences that are applied or made available, and the ways of stating and employing specific inferences, do not form parts of the present invention. Such inferences are recognized to be tools which can be freely and flexibly designed by those skilled in the art to have the appropriate user-specific applicability.

By way of example, and given a supply of pre-inference information from block 32 on line 62 which suggests the finding of, say, five infarct sites (e.g., number-weighted sections in the four-quadrant picturing of the left ventricle of the heart), an appropriate inference might include a statement that such a found pattern of infarct sites is most probably an indication of a single larger infarct. It might further include a statement that such a single infarct has several internal regions characterized by different densities, or by different other qualities, and that these matters, while recognized as being contributors to a single infarct, ought to be differentiated pictorially in the output display. Differing densities, for example, could be directly related to the score weighting (number valuding) practice mentioned above in relation to the operation of APPLY RULES block 32.

It is known for example that after a heart attack there may be regions of heart muscle in the wall of the ventricle that appear electrically dead, and fail to contract. Large groups of heart muscle cells may be stunned or hibernating and at a later time recover electrically and be stimulated to contact. Conversely, a fresh new myocardial infarct in an adjacent region can occur from another occlusion of a coronary artery supplying this region and the apparent center, density and size of the infarct may shift over time. This knowledge in both cases can lead to instructions from the APPLY INFERENCES block for changes in infarct size, density and location to be presented by the output display.

From the activity which takes place in the APPLY INFERENCES block, the computer generates the final post-inference interpretation output signal that goes to display structure 48. This output signal is suitably constructed, in any one of many conventional and well-known manners, to instruct the display apparatus how to create an appropriate visual marker on a pictorial representation of the heart. In the system and method embodiments now being described, the interpretation output signal takes the form of a digital data stream numbers (or vectors)—interpretation score numbers associated locationally with each of the twelve left-ventricle sections mentioned above. Appropriate (and conventional) source data describing how to picture the heart per se, from as many different vantage points as are determined to be desirable, can readily be supplied from the computer in the system to the display apparatus. Such heart-picturing source data is preferably rich enough in content to allow the creation of a heart image which is most likely to characterize, with substantial accuracy, a particular selected subject's actual heart anatomy. For example, heart-imagery data can be drawn from such source data specifically in relation to, and by inference from, subject-specific physiological/anatomical data like that contained in block 52.

Talking now a bit about how an interpretation output signal—the stream of locationally associated numbers mentioned above—can be employed to create a pictorial display in the display apparatus, the following outline of steps describes our current, preferred way of doing this:

(1) Take as input, for each of the mentioned twelve left-ventricle sections, the vector that corresponds to the interpreted output. This vector corresponds, for example, to the amount of infarction in a specific 1/12 section of the left ventricle of the heart. '0' corresponds to no infarct present, and '8' corresponds to the entire region being infarcted;

(2) Take as input, for each of these twelve sections, information in the interpretation output signal data stream that represents the associated spatial coordinate representation of the heart;

(3) Subdivide each of the twelve left-ventricle segments into approximately eight regions;

(4) In a Mercator maplike projection, locate which sub-segment within each major segment is closest to the terminus of a coronary artery branch;

(5) In each segment with a non-zero associated vector element, "fill in" the number of sub-segments corresponding to the value of the vector element. Start this "filling-in" process at the sub-segment located by step (4), and work outward until the appropriate number of sub-segments are "filled";

(6) Apply a clustering process to "pull" all the filled sub-segments together. The clustering algorithm moves the filled sub-segments towards a center region that corresponds to the densest cluster of filled sub-segments;

(7) Determine whether and how to use color, or other, pictorial variation to differentiate different regions; and (8) Use a spatially invariant two-dimensional filter to make the marked region look more connectedly uniform.

The output display apparatus, in possession of interpretation information arrived at by implementation of the eight steps just generally described, furnishes the desired pictorial output imagery—imagery coupling a generally representational view of the heart (from a selected point of view) with visual markers (based upon the numbers just discussed above) which picture in place, and with substantial configurational accuracy, the selected, found condition or conditions.

Figure 6A:
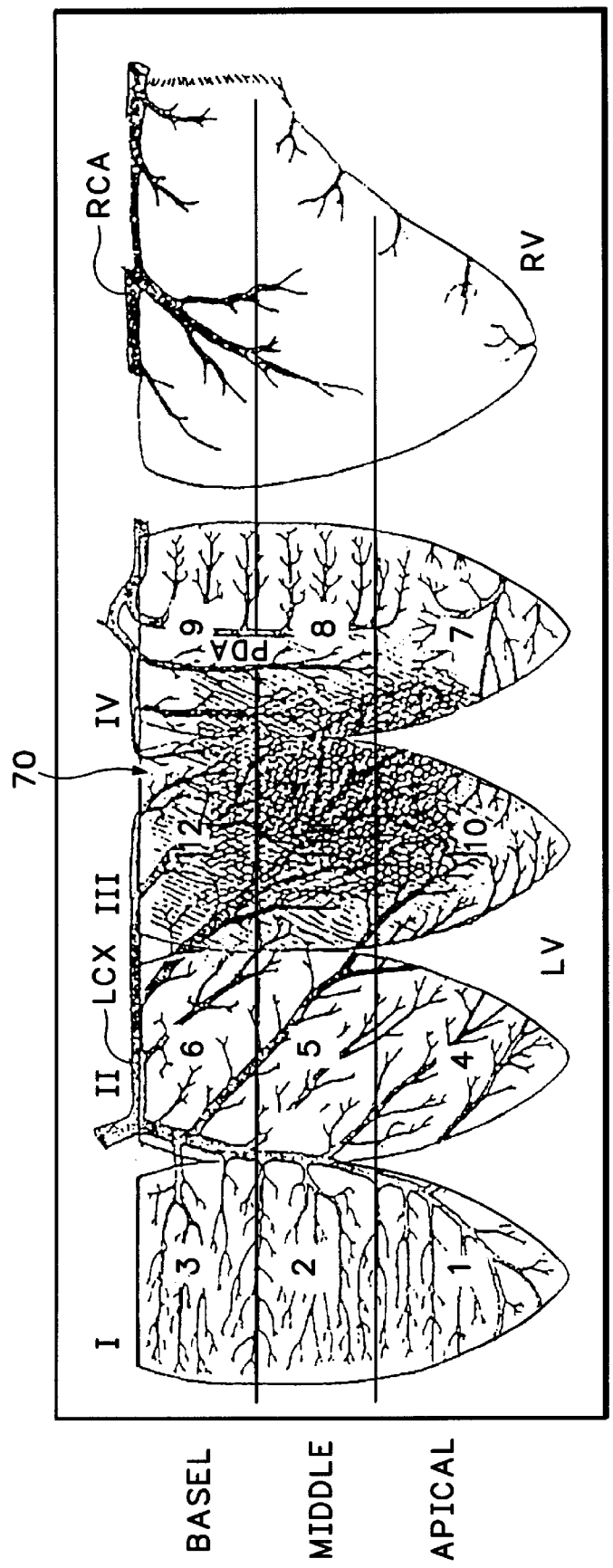
FIG. 6A is a view showing a map-like Mercator output display that illustrates one convenient output format for providing pictorial output information in accordance with the method and system of the present invention. This view shows a single medium-size infarct that extends over certain segments in two quadrants of the left ventricle in a heart.
Figure 6B:
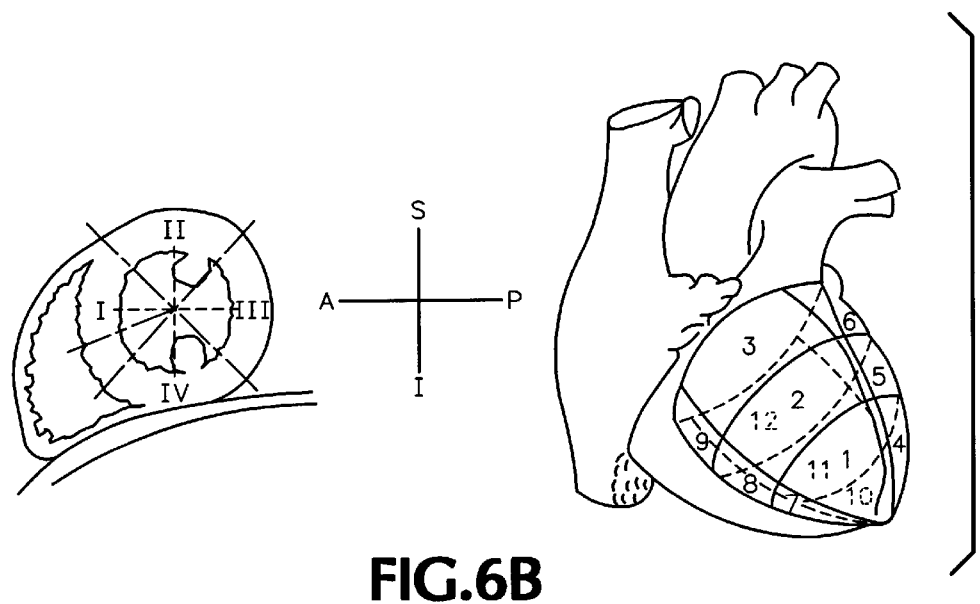
FIG. 6B presents two diagramatic, fragmentary and sectional views of a typical heart. These views are preferably displayed along with a view like that provided in FIG. 6A to act as an aid in understanding the orientation of information conveyed by a FIG. 6A-type display.

FIGS. 6A, 6B, 7A and 7B illustrate several characteristics of two different output displays which might be created by an interpretation output signal fed to display structure 48. FIG. 6A shows one type of display which we have found to be very informative and useful. FIG. 6B shows two images which are preferably included with a display like that presented in FIG. 6A in order to aid, for example, in establishing point of view.

In the display of FIG. 6A, there is pictured a Mercator map-like representation, generally showing actual heart structure, and presenting four left-ventricle quadrants labeled I, II, III and IV. These four quadrants are divided each into three segments—basal, middle and apical. These are the sectioned quadrants that were mentioned earlier. Quadrants I, II, III and IV are, respectively, the Anteroseptal quadrant, the Anterosuperior quadrant, the Posterolateral quadrant and the Inferior—quadrant.

Immediately to the right of this left-ventricle display is a singular display of the right ventricle.

Letter legends which appear in FIG. 6A have the following meanings:

LCX—left circumflex coronary artery
LAD—left anterio descending coronary artery
LV—left ventricle
PDA—posterior descending coronary artery
RCA—right coronary artery
RV—right ventricle Appearing generally at 70 in FIG. 6A, and extending over two quadrants and six segments in the left ventricle, is a moderate-size single infarct which has been detected and characterized by the preferred method and system of this invention. This infarct has regions which are distributed in quadrants numbers III and IV, and in the segments numbered 7, 8, 9, 10, 11 and 12.

Figures 7A, 7B:
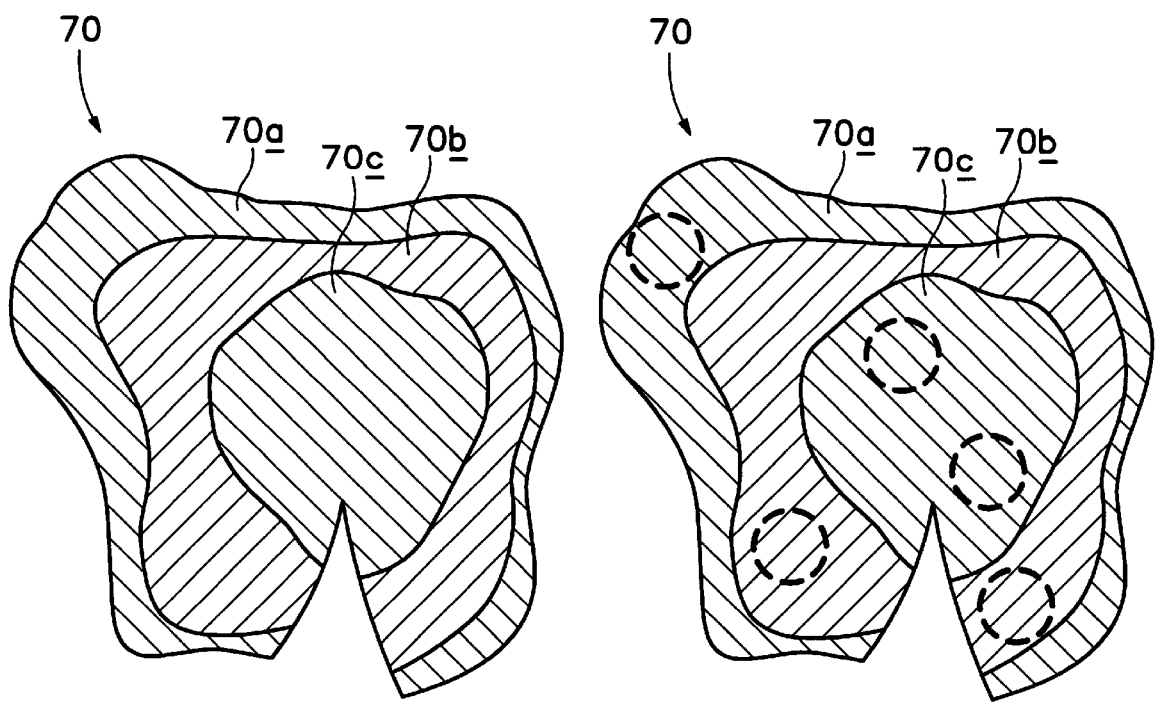
FIG. 7A isolates and enlarges, for separate illustration purposes, the infarct shown in FIG. 6A. This illustrated infarct is pictured as including three differently shaded regions, which regions relate to three regions of differing infarct density.
FIG. 7B is very much like FIG. 7A, except that it contains (additionally) five, bold-line dashed circles. These circles represent certain underlying infarct-site information from which the display of the single infarct of FIGS. 6A, 7A, 7B, has been inferred in the preferred practice of the present invention.

Infarct 70 is pictured as including three regions which have different densities. These regions are further identified more clearly in FIG. 7A which isolates infarct 70 from other visual information, and clearly shows these three areas at 70a, 70b, 70c. Infarct 70 as pictured in FIG. 7A is not shown with exactly the same shape with which it is seen in FIG. 6A. Different graphical approaches can be used to differentiate three mentioned areas, and what is pictured in FIG. 7A is intended to symbolize differentiation by color. The three regions pictured illustrate a pattern wherein infarct density generally increases progressing inwardly from the outer boundaries of the infarct—from region 70a to region 70c. One can see clearly in FIGS. 6A, 7A that the visual representation of infarct 70 includes a picturing of its outer perimeter, a picturing of its probable location in the left ventricle wall of the heart, its general orientation and size, and one aspect of its interior character, namely, differentiated density.

This image of infarct 70, as created during a representative, normal functioning of system and method 20 as so far described, is an image very closely picturing the actual "source" infarct in the heart. It is an image which has resulted from the operation of system and method 20 wherein the final interpretation output imagery results essentially from examination of substantially the actual electrical signature of the infarct presented at input 22 in the input ECG waveform data.

Looking now at FIG. 7B, this figure includes, in addition to the same picture of infarct 70 that is presented in FIG. 7A, an overlapping image of five dark-dashed circles. These five circles illustrate what might well be the underlying pre-inference interpretation of detected infarct presence—i.e., the mid-stage, pre-inference interpretation which emerges from APPLY RULES block 32. In a system which is not equipped to apply inferences as a part of the interpretation activity, output information can be directly taken from the APPLY RULES block. This information will form an interpretation output signal which will instruct the graphics structure to create, essentially, that part of the heart-condition imagery which is pictured in FIG. 7B as dashed-line circles.

The operational description offered so far herein regarding system and method 20 has focussed particular attention on the finding and depicting of infarct information. Functionality with regard to other findable and picturable conditions, such as localized ectopic foci and ischemia sites, is very similar, and is based upon the same sorts of interpretation stages and logics as those described for infarct assessment. The specific pictorial output displays which are shown in FIGS. 6A–7B, inclusive, can be revisualized, accordingly, to describe what one might typically expect to see as an output display covering one of these other kinds of heart conditions. Text, or other appropriate indicators, selectable freely at the choice of the designer/user, will preferably be included somewhere in each output display, or be a part of the pictorial elements in the display itself, to identify the specific category or categories of a pictured condition.

It should be very clear now from a reading of the description which has just been given for the invention as such is pictured in FIG. 4, that the present invention in its preferred form offers a clear capability for examining a subject's ECG waveform data to create a highly informative pictorial display that can identify the natures, locations, orientations, sizes, etc. of any one of a number of selected heart conditions, such as those which have been specifically mentioned so far herein. The pictorial identification thus furnished significantly surpasses the information-giving abilities of conventional graphs and tables of numbers. The level of interpretation capability is substantially as wide in range as are the wishes of the individual application designer/user. The choice of rules for interpretation which is made, the ways in which those rules are elected to be applied, and the range and ways of applying inferences, define the selectable versatility with which this invention can perform. In some applications, only certain very simple displays, such as the dashed circles illustrated in FIG. 7B, may be all that is wanted. With regard to the creation of rules and rule sets, and the defining of inferences to be used, these tasks are well within the skills levels of trained electro-cardiologists. Given this understanding, and recognizing the "definitional" versatility and flexibility provided by the system and method of this invention, it is fair to assume that different electro-cardiologists might well create specifically different rules, criteria and inferences to implement and practice this invention. Such differences, however, will not result in significantly different output displays.

The preferred form of the invention, including all of the features and characteristics pictured in and described with respect to the full content of FIG. 4, offers a very high-level, highly detailed informational display presentation. In a situation where the system and method of the invention are modified to either one of the two alternative forms mentioned earlier, wherein received information arrives in the category of a pre-computer-processed interpretation output signal, the resulting pictorial output display is also highly detailed—a little bit more so typically in the case where the received information is post-inference information than in the case where it is pre-inference information.

Considering certain other modifications of the invention, one such other type involves eliminating the input of hypertrophy information. This is a modification approach which can be made with respect to each of the several earlier-described forms/aspects of the invention. Elimination of hypertrophy information, of course, changes the range of information content which is made available to the APPLY RULES block, and thus changes the range of prospective information content in the finally used interpretation output signal (pre-inference and/or post-inference).

Figure 8:
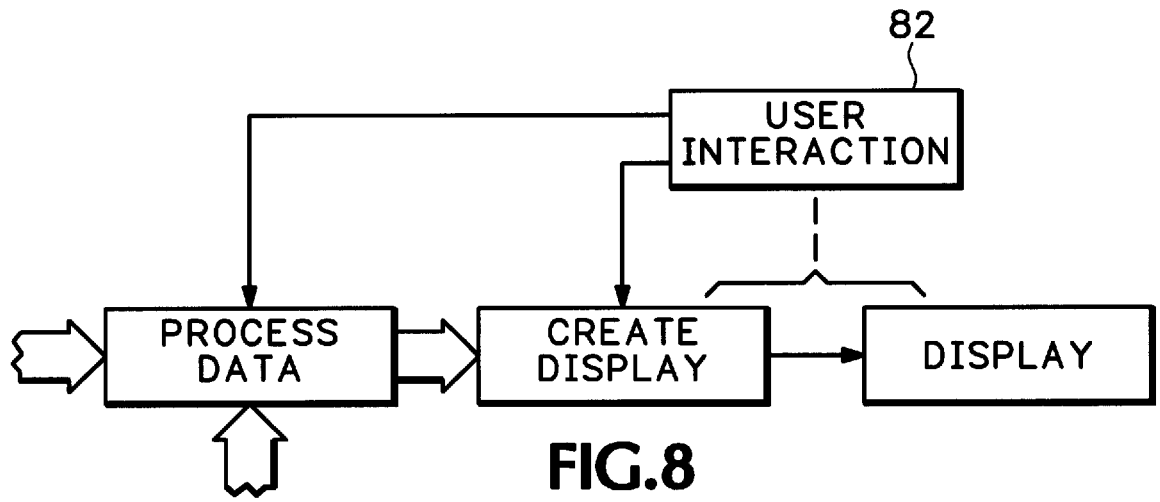
FIG. 8 is a fragmentary block diagram which pictures a system and a method modification that relates to user interaction respecting a pictorial output display.
Figure 9:
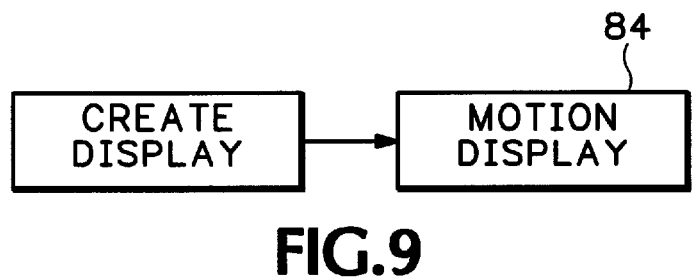
FIG. 9 is a fragmentary block diagram illustrating a modification of the system and method of the present invention wherein a motion-type output display is provided.
Figure 10:
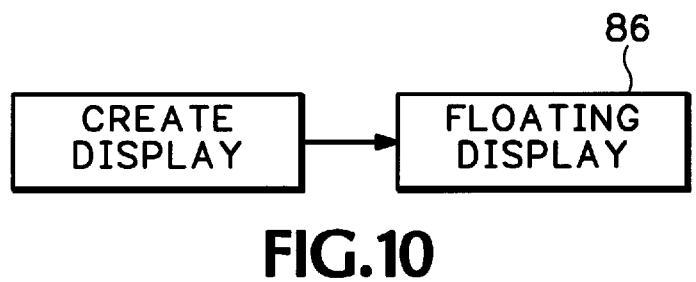
FIG. 10 is another fragmentary block diagram, here illustrating the capability of the system and of its associated method to create a floating, real-image display.

Several other modifications are illustrated in FIGS. 8, 9 and 10.

FIG. 8 shows a modification wherein user interaction, symbolized by a block 82 labeled USER INTERACTION, can enable a user of the system to manipulate, as by moving, rotating, etc. an output display result. Block 82 is also referred to herein as user interaction structure. Such user interaction can come about in any one of a number of conventionally available ways, including (1) use of a joystick, (2) use of a data glove, (3) use of spatial hand-motion sensors distributed and located in the immediate vicinity of the display, and (4) in any other conventionally doable manner. The specific ways of incorporating such user interaction can be drawn from various conventional, prior art techniques currently available for enabling the manipulation of computer-generated pictorial displays. FIG. 8 recognizes schematically that appropriate interaction will probably typically include operative interaction in the system both with the processing of interpretation data, and with the actual final creating of the visible pictorial output display. These are conventionally understood interactions.

FIG. 9 illustrates a modification of the system including a display output block 84 which is labeled MOTION DISPLAY. This figure pictures a system in which output information from the computer is capable of driving/promoting motion output imagery. Conventional techniques for creating such a motion display are available and may be used effectively here.

FIG. 10 illustrates a modified system wherein the output pictorial display takes the form of a floating real image, for example, a three-dimensional-appearing image which floats freely in space. Block 86, labeled FLOATING DISPLAY, represents this kind of modified output display. Various conventional imagery output display systems are available which possess such a capability.

By way of further illustration regarding the output display, it may be desirable in certain instances to present a marked view of the heart wherein the heart structure per se is pictured with a certain level of transparency. Such a view can help a user/observer effectively "see through" the heart to gain a better perspective about the three-dimensional distribution of the found heart condition or conditions. Further, another category of output display can include a visual representation of the physical anatomical environment that surrounds the heart. Many different points of view can be chosen for the display. For example, there may be applications where it is desirable to present pictorial output information in the context of either or both a left anterior oblique view and/or a right anterior oblique view.

Figure 11A:
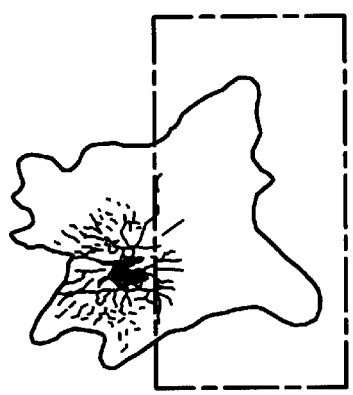
FIGS. 11A, 11B, 11C are stylized diagrams which illustrate the capability of the method and system of the present invention to display, comparatively, a selected heart condition that has changed in size and shape over a period of time.
Figure 11B:
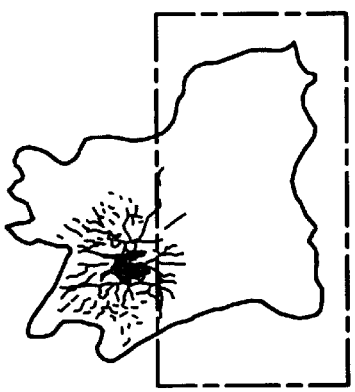
Figure 11C:
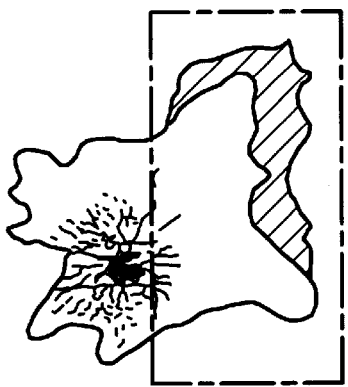

Describing now the remaining drawing figures, FIGS. 11A, 11B generally show an infarct 90 which, in FIG. 11A (created at one point in time), has a certain perimeter shape, and in FIG. 11B (created at a later point in time) has a different and larger perimeter shape. FIG. 11C illustrates use of the invention to present an overlap view (of FIGS. 11A, 11B), which view highlights regions (shaded) of perimeter change.

Figure 12A:
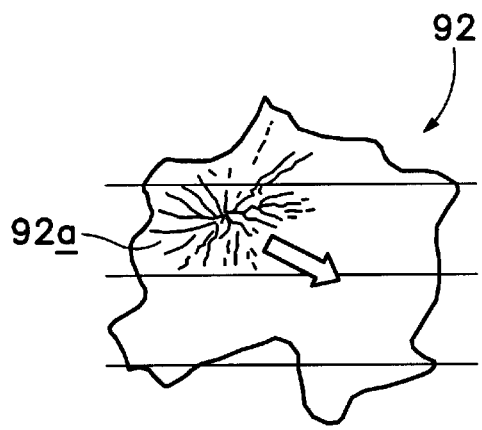
FIGS. 12A, 12B present two time-displaced output displays of a heart condition whose geographic center of interest (for example, density) has migrated.
Figure 12B:
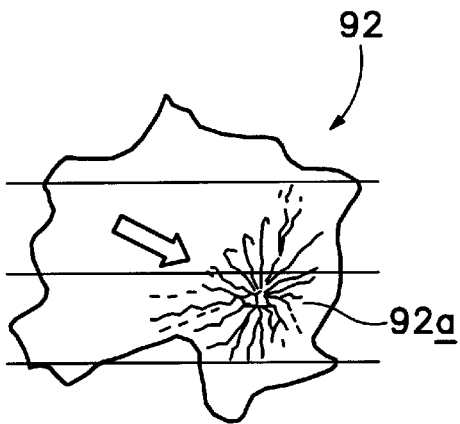

FIGS. 12A, 12B illustrate earlier and later views, respectively, of an infarct 92 having, for example, a center of density 92a which has effectively migrated over time.

Figure 13A:
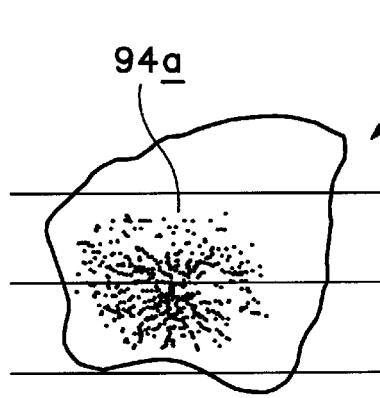
FIGS. 13A, 13B present two time-displaced output displays of a selected heart condition having a "center of presence", so-to-speak whose geographic extent and central density have modified with time.
Figure 13B:
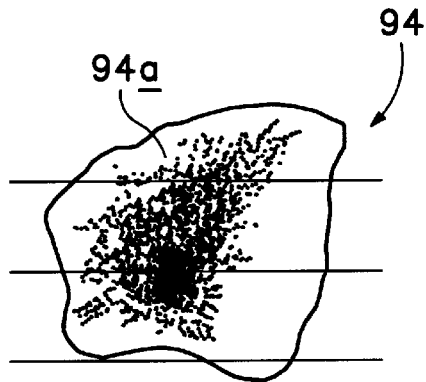

FIGS. 13A, 13B illustrate, respectively, earlier and later pictorial views of an infarct 94 having a central density feature 94a which has changed over time.

FIGS. 14A, 14B illustrate, respectively, earlier and later pictorial displays of an infarct 96 which has several internal differentiable regions of interest (such as density regions) that have changed over time. In FIG. 14A, and using one set of respective shading lines, the infarct as pictured there has differentiable regions labeled a, b, c. FIG. 14B, using respectively different line-shading characteristics, shows infarct 96 as having differentiated internal regions marked d, e, f Changed regions d, e, f in FIG. 14B relate to regions a, b, c, respectively, in FIG. 14A.

FIGS. 15A, 15B, using the visual aid of a single three-dimensionally appearing cube, illustrate, through the device of a shaded plane of intersection with this cube, two different display-presentation points of view which the system and method of the invention can easily offer.

The system and method of the present invention thus offer a unique visual approach to cardio-interpretation. Management of, and extraction of information from, a subject's ECG data pursuant to the invention effectively offer an interpretation environment which bases interpretation on a substantially faithful rendering of the electrical signature of a selected heart condition. Computer processing, the using of tailored rules for interpretation, and preferably also the using of knowledge-based inferencing, contribute to the creating of an information-rich pictorial display. Adding to these things the using of physiological/anatomical reference data, and the using also of subject-specific physiological/anatomical and medical-history data, lead to an especially useful output display.

Several modifications of the invention have been mentioned herein which illustrate (though not exhaustively) the range of options for implementation. Within the settings of each of these modifications, the designer/user can choose (as appropriate to the specific modification contemplated) either to use or not to use hypertrophy information, general reference physiological/anatomical data, and subject-specific physiological/anatomical and medical-history data. The subject-specific physiological, etc. data will most commonly be furnished to the system at the time of furnishing subject-specific ECG-related data. An output interpretation output signal can have either a pre-inference or a post-inference characteristic. Input ECG-related data can be acquired in a wide variety of ways. Output pictorial displays can easily take a number of different forms. In addition to effecting a pictorial output display, the system and method of the present invention can also do other things, such as create a text report, transmit output information to a remote location for study at that site, activate a medical response action such as the administering of a medication, sound of an alarm, and much more.

What is claimed is:

1. An electrocardiointerpretation system comprising
input structure constructed to receive a subject's ECG-related data, and
computer structure operatively connected to said input structure, adapted to interpret received data to focus attention upon a selected heart condition if such is found to exist in the subject's heart as reflected in that data, said computer structure being operable, with respect to such a focus, to create an interpretation output signal which is configured to effect a pictorial, heart-representational visual display that bears one or more marker(s) that is(are) interpretable to convey selected medical information about such a found condition.

2. An electrocardiointerpretation system comprising
input zone structure constructed to receive a computer-prepared cardiointerpretation signal of a type which has been computer-prepared in relation to a specific subject's ECG waveforms, and which includes medical-character information relating to a selected kind of heart condition, and
a pictorial display subsystem operatively connected to said input zone structure, operable, on the latter's receiving such a prepared interpretation signal, to produce, on the basis of information contained in that interpretation signal, a pictorial output display of the selected condition pictured on a generally representational view of at least a portion of the heart.

3. An electrocardiointerpretation system comprising input structure constructed to receive a subject's ECG-related data, computer structure operatively connected to said input structure, adapted to interpret received data in order to focus attention upon a selected heart condition if such is found to exist in the subject's heart as reflected in that data, and pictorial display structure operatively connected to said computer structure, operable, on the basis of information contained in such a focus, to create a pictorial display illustrating any such condition.

4. A medical, heart-related condition-display system comprising first data-input structure adapted to acquire, from any suitable source, a first collection of subject-specific, ECG-related data, and computer-like data-processing structure operatively connected to said first data-input structure, operable, in connection with acquisition by the first data-input structure of such a first collection of data, to perform, on and with respect to data contained in that first collection, interpretation analysis, thus to create a pictorial, heart-representational, visual-pictorial-display-enabling interpretation output signal which is configured to effect a pictorial, heart-representational visual display that bears one or more marker(s) that is (are) interpretable to convey selected medical information about a (or plural) specific, physical, three-dimensional, site-located condition(s) existing within the related subject's heart.

5. The system of claim 4 which further includes a second data-input structure operatively connected to said data-processing structure, adapted to acquire (also from any suitable source) a second collection of data, which second collection includes expressions of certain selected interpretation protocols that are applicable, generally, to data of the kind contained in the first-mentioned collection of data to enable and define the above-mentioned interpretation analysis.

6. A medical, heart-related condition-display system comprising first data-input structure adapted to acquire, from any suitable source, a first collection of subject-specific, ECG-related data, computer-like data-processing structure operatively connected to said first data-input structure, operable, in connection with acquisition by the first data-input structure of such a first collection of data, to process the data contained in that first collection so as to create a visual-pictorial-display-enabling interpretation output signal, and pictorial display structure operatively connected to said data-processing structure, adapted to receive such an output signal, and operable, on receiving the same, to create therefrom a pictorial, heart-representational visual display that bears one or more visual marker(s) that is (are) interpretable to convey selected medical information about a (or plural) specific, physical, three-dimensional, site-located condition(s) existing within the related subject's heart.

7. The system of claim 6 which further includes a second data-input structure operatively connected to said data-processing structure, adapted to acquire (also from any suitable source), a second collection of data, which second collection includes expressions of certain selected interpretation protocols that are applicable, generally, to data of the kind contained in the first-mentioned collection of data to enable, allow and define the creation of the above-mentioned interpretation output signal.

8. The system of claim 5 or 7, wherein the expressions of selected interpretation protocols included in the second collection of data take the form of interpretation rules, and wherein, as a predecessor activity in relation to creating the mentioned interpretation output signal, a selected portion (or portions) of these rules is (are) applied by said data-processing structure to data contained in the first collection of data.

9. The system of claim 8, wherein the second collection of data further includes a first, selected body of general, plural-subject-based, anatomical and physiological subdata, which first body of subdata is, in relation to predecessor activity regarding creation of the mentioned interpretation output signal, examined by said data-processing structure with respect to data contained in the first collection of data.

10. The system of claim 9, wherein the second collection of data still further includes a second, selected body of single-subject-specific, anatomical, physiological and medical-history subdata, which second body of subdata is, in relation to predecessor activity regarding creation of the mentioned interpretation output signal, examined by said data-processing structure with respect to data contained in the first collection of data.

11. The system of claim 10, with respect to which the mentioned second selected body of single-subject-specific subdata includes information relating to one or more of the several characteristics selected, for example, from (but not limited to) the group consisting of subject height, weight, sex, race, torso configuration, heart size, heart location and heart orientation.

12. A computer-based, heart-related, medical-assistant system comprising first data-input structure operatively connectable, directly or via mesne communication media, to a subject to acquire therefrom an ECG data signal containing a first collection of subject-specific ECG-related data, which data potentially includes data-signal components that are directly related to one or more selected, volume-occupying, definitively spatially located, heart conditions disposed within the physical boundaries of the subject's heart, and computer data-processing structure operatively connected to said first data-input structure, adapted to receive from that input structure at least a portion of the data contained in the mentioned collection of data, said data-processing structure being operable, in relation to receiving such a portion, to create an interpretation output signal which is structured to effect a pictorial, anatomically-representational, map-like, visible output display that pictures the subject's heart in a manner including representational imagery that contains visible, spatially-differentiated markings which identify, inter alia, the presence(s), character(s), size(s), boundary(ies) and/or location(s), if any, of such selected heart conditions.

13. The system of claim 12 with respect to which such mesne communication media includes a medium (or a combination thereof) selected from the group consisting, inter alia, of (a) a memory structure containing a pre-acquired bank of subject-specific ECG data, (b) a telephone line (conductive, optical or other) connected to a source of subject-specific ECG data, (c) appropriate receptor structure designed to acquire propagated electromagnetic radiation, and (d) any appropriate communication connection to one or more "locations" sited in the Internet and containing subject-specific ECG data.

14. The system of claim 4, 6, 12 or 13 with respect to which the mentioned condition(s) is(are) associated with one or more of the several phenomena selected from the group consisting of myocardial infarcts (old, acute and subacute), ventricular mass, hypertrophy, localized ischemia and ectopic foci.

15. The system of claim 4, 6 or 12 with respect to which the mentioned interpretation output signal is configured to effect, selectively, both a static and a motion display, including a floating, real-image display.

16. The system of claim 15 which further includes user-interaction structure operatively associated with other structure in the system, and operable selectively by a system user to interact with a display which is enabled by the mentioned interpretation output signal.

17. An electrocardiointerpretation method comprising
acquiring a subject's ECG-related data,
interpreting such acquired data utilizing a computer to produce focus upon a selected heart condition if such is found to exist in the subject's heart as reflected in the acquired ECG-related data, and
on the basis of such focus, creating a pictorial display illustrating the heart condition which is the source of that focus.

18. The method of claim 17, wherein said interpreting includes applying selected particularized rules for interpretation chosen for this purpose from a library of rules, and on the basis of certain selection-defining characteristics of the acquired data.

19. The method of claim 17, wherein said interpreting includes applying selected, particularized inferences chosen for this purpose from a library of inferences, and on the basis of certain selection-defining characteristics of the acquired data.

20. A heart-related medical-assistant method comprising
acquiring a collection of ECG-category data sourced ultimately from a specific living subject,
analyzing that data under the control of a computer to detect and characterize a selected category of heart condition, and
further under the control of a computer, effecting a representational pictorial display of such a selected condition pictured graphically in place relative to the associated anatomical structure of the heart.

21. The method of claim 20, wherein said analyzing includes analyzing whether the P-wave is responsible for driving the existence of the QRS components of the data.

22. The method of claim 20 or 21, wherein said analyzing includes assessing the data to characterize heart conduction characteristics, and on the basis of that assessing, applying interpretation rules selected for application on the basis of the assessed conduction characteristics.

23. A computer-based, medical-assistant method for monitoring and observing selected, physical, three-dimensional heart conditions in a subject's heart comprising the steps of acquiring, ultimately from a subject, ECG-related data potentially including components which are directly related to one or more selected, volume-occupying, definitively spatially located, heart conditions disposed within the physical boundaries of the heart, and
from such data, producing an interpretation output signal which is structured to effect a pictorial, anatomically-representational, visual output display that pictures the subject's heart in a manner including representational imagery that contains visible, spatially-differentiated, three-dimensional-characteristic markings which identify, inter alia, the presence(s), character(s) and/or location(s), if any, of such selected conditions.

24. The method of claim 23, wherein the assistance being provided by the method relates to selected conditions including, inter alia, myocardial infarcts (old, acute and subacute), ventricular mass, localized ischemia, ectopic foci and hypertrophy.

25. A computer-based medical-assistant method for monitoring and observing selected conditions in a subject's heart comprising the steps of acquiring ECG data from a subject, which data potentially contains components that are related to one or more such condition(s),
computer-processing that data, along with other information derived from (a) certain subject-specific physiologic data, and (b) selected rules associated with an act (or acts) of heart-specific condition interpretation to create an interpretation output signal, and
as an outcome of said computer processing, producing a pictorial, map-like output display that identifies the presence(s), character(s) and/or location(s), if any within the subject's heart, of a condition, or conditions, therewithin that are responsible for the existence, in the ECG data, of such components.

26. A medical-assistant method comprising
providing an electronic interpretation-based display structure,
equipping that structure so that it effectively has an operative connection to a collection of heart-related data, including subject-specific heart-related data,
utilizing such electronic structure, performing an interpretation regarding such collection of data, and
on the basis of said performing, generating a pictorial, representational display of the subject's heart, with such display including visual markers that are associated with particular regions of selected medical interest relative to the heart.

27. A computer-based medical-assistance method for observing a selected subject's heart to obtain information about a selected type of condition which might exist at one or more physical location(s) in the heart, said method comprising acquiring, ultimately from a chosen subject, a collection of data which is based upon patient-specific ECG data,
supplying that collection to an interpretation system which includes a computer,
within that system, performing an interpretation of such supplied data to create an interpretation output signal which is capable of effecting the creation of a visual, representational, pictorial display of at least a portion of the selected subject's heart, with such display being decorated with visual markings that symbolize the existence(s) in that heart portion of such a type of selected condition, and utilizing such an interpretation output signal, effecting such a display.

28. A computer-implemented electrocardiointerpretation method comprising accessing a first collection of data which is derived from selected, subject-specific ECG data, accessing a second collection of data which includes expressions of certain selected interpretation protocols applicable, generally, to data of the kind contained in the first collection, computer-correlating at least certain selected portions of the data in the second collection to at least certain selected portions of the data in the first collection to establish a correlation nexus between such selected portions in the two collections of data, and following such establishing, creating an interpretation output signal which is capable of effecting a pictorial display that illustrates the presence(s) and location(s) of selected conditions resident in the heart.

* * * * *